US012799538B2

(12) United States Patent
Bhaduri-McIntosh et al.

(10) Patent No.: US 12,799,538 B2
(45) Date of Patent: Nov. 17, 2026

(54) COMPOSITIONS AND METHODS FOR PREDICTING SUSCEPTIBILITY OF CANCERS TO SYNTHETIC-LETHAL THERAPIES

(71) Applicant: University of Florida Research Foundation, Inc., Gainesville, FL (US)

(72) Inventors: Sumita Bhaduri-McIntosh, Gainesville, FL (US); Michael McIntosh, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 1260 days.

(21) Appl. No.: 17/616,087

(22) PCT Filed: May 27, 2020

(86) PCT No.: PCT/US2020/034636
§ 371 (c)(1),
(2) Date: Dec. 2, 2021

(87) PCT Pub. No.: WO2020/247220
PCT Pub. Date: Dec. 10, 2020

(65) Prior Publication Data

US 2022/0298579 A1 Sep. 22, 2022

Related U.S. Application Data

(60) Provisional application No. 62/856,301, filed on Jun. 3, 2019.

(51) Int. Cl.
*C12Q 1/6886* (2018.01)

(52) U.S. Cl.
CPC ..... *C12Q 1/6886* (2013.01); *C12Q 2600/106* (2013.01); *C12Q 2600/158* (2013.01)

(58) Field of Classification Search
CPC ............ C12Q 1/6886; C12Q 2600/106; C12Q 2600/158
See application file for complete search history.

(56) References Cited

PUBLICATIONS

Keung (Journal of clinical medicine 8.4 (Mar. 30, 2019): 435) (Year: 2019).*
Chakraborty (Iscience 2 (2018): 123-135) (Year: 2018).*
Lin (Acta Biochim Biophys Sin 43.11 (2011): 916-917) (Year: 2011).*
Haupt (Journal of molecular cell biology 9.1 (2017): 53-61) (Year: 2017).*
Wei (Stem cells 32.10 (2014): 2571-2582) (Year: 2014).*
Tang (Oncology letters 16.2 (2018): 2453-2461) (Year: 2018).*
Liu (International journal of biological sciences 15.3 (2019): 636) (Year: 2019).*
Huang (Tumor Biology 35.10 (2014): 9927-9934) (Year: 2014).*
Ji (Frontiers in bioscience: a journal and virtual library 14 (2009): 2904) (Year: 2009).*
Zhen (Genetics in Medicine 17.7 (2015): 569-577) (Year: 2015).*
Fogelman (Anticancer research 31.4 (2011): 1417-1420) (Year: 2011).*
Santuario-Facio (Molecular Medicine 23.1 (2017): 101-111) (Year: 2017).*
Al Kubaisy (Expert opinion on therapeutic targets 20.9 (2016): 1035-1043) (Year: 2016).*
Rehman (Nature Reviews Clinical Oncology 7.12 (2010): 718-724) (Year: 2010).*
Wang (Oncogene 38.14 (Dec. 7, 2018): 2451-2463) (Year: 2019).*
International Search Report issued for PCT/US2020/034636, mailed Oct. 23, 2020.
Kawahara, et al. Candidate synthetic lethality partners to PARP inhibitors in the treatment of ovarian clear cell cancer. Biomed Rep. 2017, 7(5): 391-399; Abstract, p. 392; p. 394, col. 2 to p. 396, col. 1.
Jeusset, et al. Developing Targeted Therapies That Exploit Aberrant Histone Ubiquitination in Cancer. Cells ePub Feb. 16, 2019, 8(2):165; Abstract, p. 3 [according to the posteddocument], p. 4, Table 1; p. 6, Table 3.

* cited by examiner

*Primary Examiner* — Neil P Hammell
*Assistant Examiner* — Kyle T Rega
(74) *Attorney, Agent, or Firm* — Thomas | Horstmeyer, LLP

(57) ABSTRACT

STAT3 (Signal Transducer and Activator of Transcription), which is overactive in two-thirds of human cancers, is shown herein to inhibit HR repair. This newly identified linkage of STAT3 to HR impairment forecasts that many more cancers, beyond just breast and ovarian cancers, are likely to be susceptible to PARP inhibitors and other synthetic lethal therapies. Also disclosed herein is a gene signature that can predict which cancers are likely to respond to therapy with PARP inhibitors and other synthetic lethal therapies.

7 Claims, 17 Drawing Sheets

Specification includes a Sequence Listing.

| Subject # | Healthy | Job's |
|---|---|---|
| 1 | 21.8 | 48 |
| 2 | 32.6 | 61 |
| 3 | 32.9 | 72.6 |

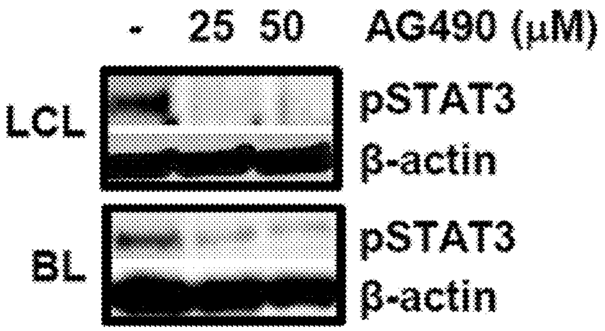
FIG. 2K
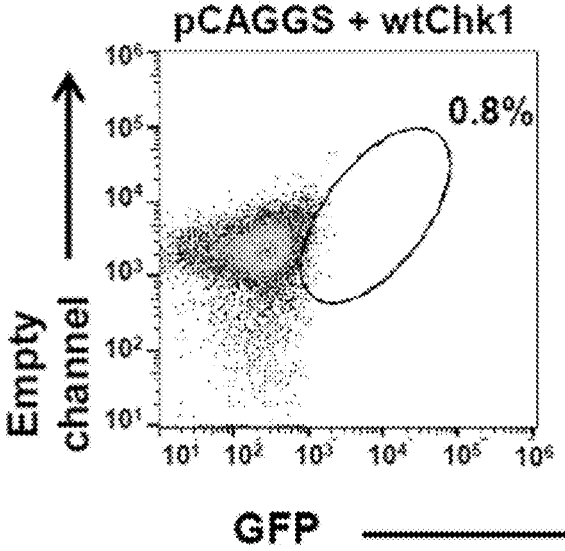
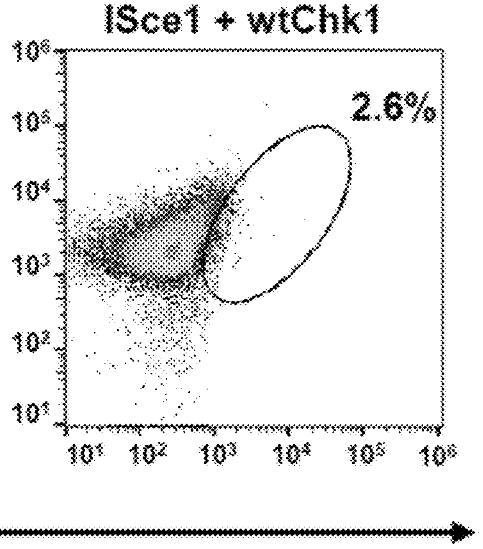
FIG. 2L
FIG. 2M
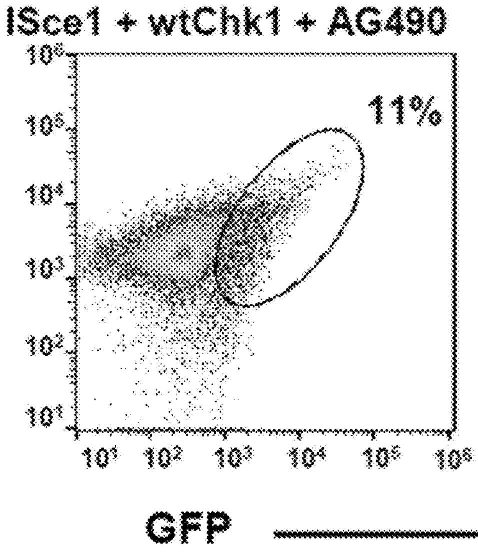
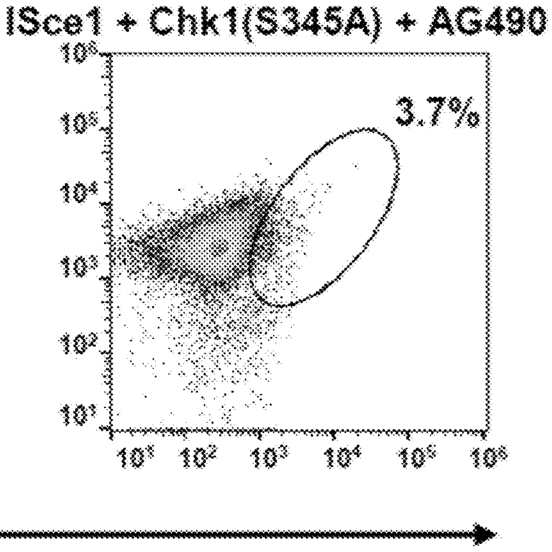
FIG. 2N
FIG. 2O

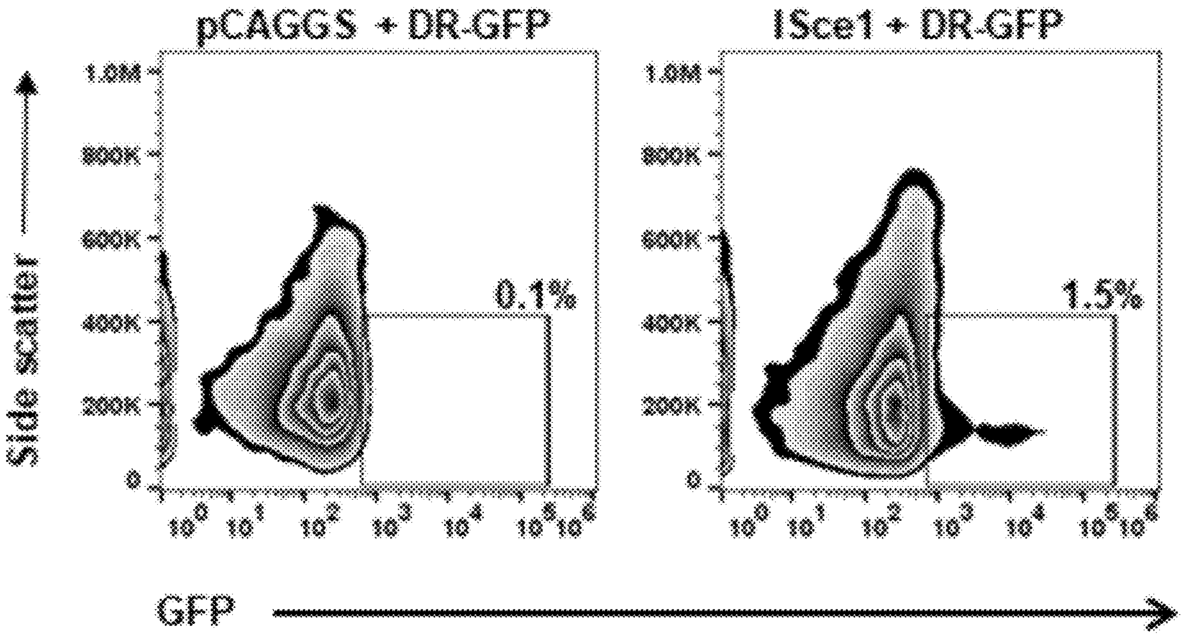
FIG. 3G
FIG. 3H
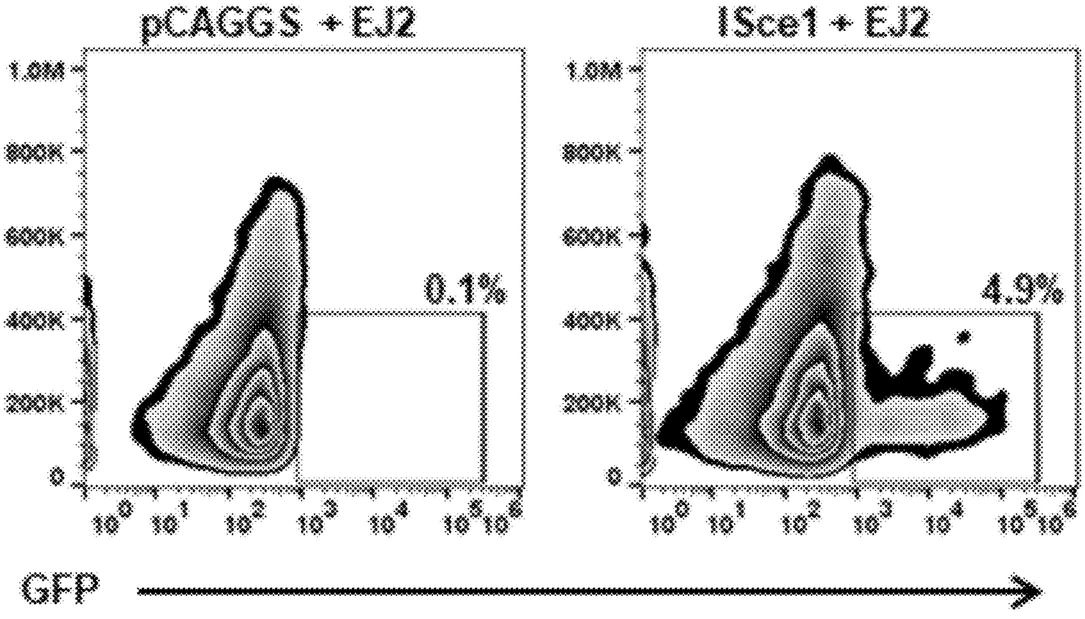
FIG. 3I
FIG. 3J

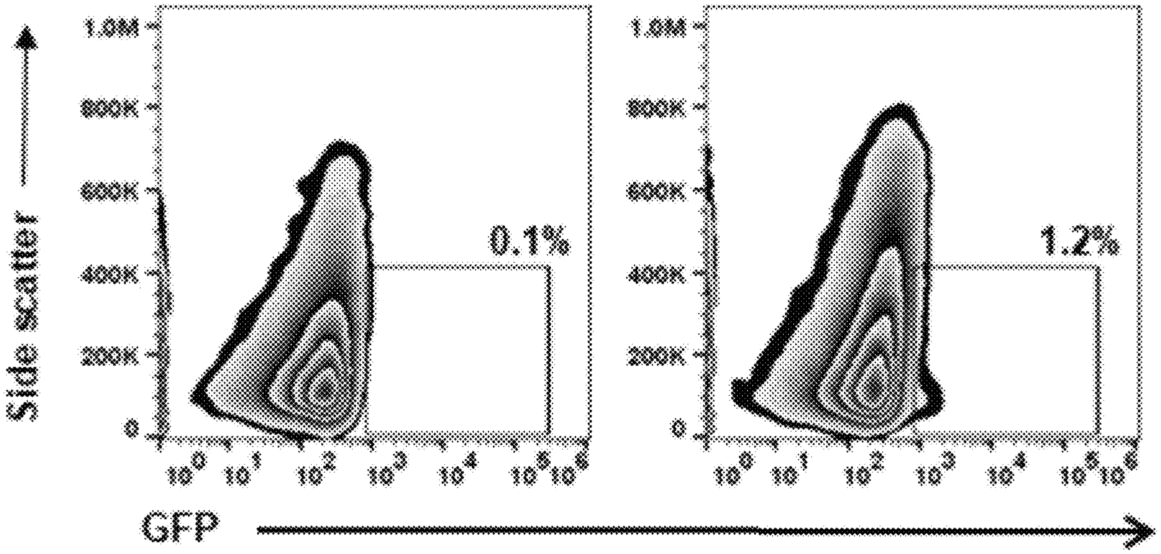
FIG. 3K
FIG. 3L
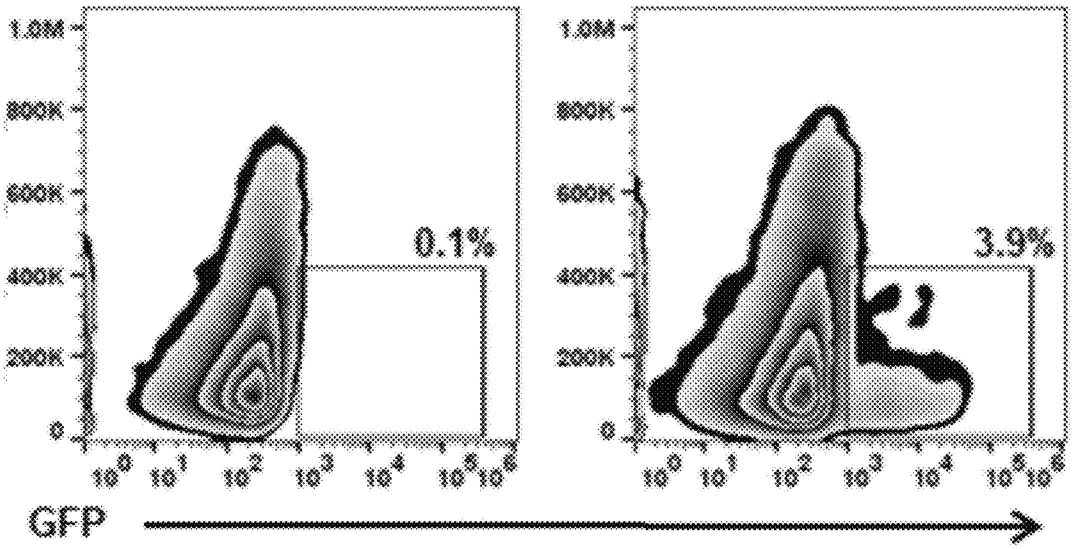
FIG. 3M
FIG. 3N

| 11 gene signature |
| --- |
| SMARCAD1 |
| PRKX |
| ZBTB40 |
| ATXN2L |
| MDM4 |
| AP4B1 |
| RBM33 |
| ATP5G2 |
| BLMH |
| GPR75.ASB3 |
| ASPHD2 |

COMPOSITIONS AND METHODS FOR PREDICTING SUSCEPTIBILITY OF CANCERS TO SYNTHETIC-LETHAL THERAPIES

CROSS-REFERENCE TO RELATED APPLICATIONS

This application is a National Stage of International Application No. PCT/US2020/034636, filed May 27, 2020, which claims benefit of U.S. Provisional Application No. 62/856,301, filed Jun. 3, 2019, which is hereby incorporated herein by reference in its entirety.

SEQUENCE LISTING

This application contains a sequence listing filed in electronic form as an ASCII.txt file entitled "222107_2500_Sequence_Listing_ST25" created on May 26, 2020. The content of the sequence listing is incorporated herein in its entirety.

BACKGROUND

DNA double strand breaks (DSB) that result from collapsed replication forks are highly genotoxic if not repaired. High fidelity repair of such DSBs is mediated by homologous recombination (HR) during S and G2 phases of the cell cycle. Because cancer is characterized by repeated and often unscheduled rounds of DNA replication, resulting in increased DNA lesions, transformed cells in particular require efficient DNA repair. Indeed, loss of DNA repair of one type makes cancer cells dependent on other repair mechanisms—and—such cancers are likely to succumb to approaches that interfere with the remaining mechanism(s) of DNA repair. This phenomenon, known as synthetic lethality, is exhibited by cancers with biallelic mutations in HR genes such as BRCA1 or BRCA2 (Ashworth, A. J Clin Oncol 26:3785-3790 (2008); Curtin, N. J. Nat Rev Cancer 12:801-817 (2012)). Synthetic lethal agents include PARP inhibitors which are a group of pharmacological inhibitors of the enzyme poly-ADP ribose polymerase. Since HR-deficient cancers depend on other modes of DNA repair including those requiring PARP, inhibition of PARP (as well as components important for other modes of DNA repair) is detrimental to their survival. This susceptibility of HR-deficient cancers to synthetic lethal approaches is commonly referred to as BRCAness and can arise from inactivating mutations or epigenetic silencing of many HR-related genes (Bast, R. C., Jr. & Mills, G. B. J Clin Oncol 28:3545-3548 (2010); Stoppa-Lyonnet, D. Eur J Hum Genet 24 Suppl 1: S3-9 (2016)).

Multiple clinical trials resulted in FDA approval of PARP inhibitors for breast and ovarian cancers with known mutations in BRCA genes (Kaufman, B. et al. J Clin Oncol 33:244-250 (2015); Kim, G. et al. Clin Cancer Res 21:4257-4261 (2015); Kristeleit, R. et al. Clin Cancer Res 23:4095-4106 (2017); Pujade-Lauraine, E. et al. Lancet Oncol 18:274-1284 (2017); Swisher, E. M. et al. Lancet Oncol 18:75-87 (2017)). However, results from preclinical studies and clinical trials indicate that PARP inhibitors may also benefit patients without BRCA mutations in whom HR is impaired (McCabe, N. et al. Cancer Res 66:8109-8115 (2006); Mirza, M. R. et al. N Engl J Med 375:2154-2164 (2016)); yet available tests that screen for HR function and known HR mutations or silencing mechanisms do not adequately predict susceptibility to PARP inhibitors.

SUMMARY

STAT3 (Signal Transducer and Activator of Transcription), which is overactive in two-thirds of human cancers, is shown herein to inhibit HR repair. This newly identified linkage of STAT3 to HR impairment forecasts that many more cancers, beyond just breast and ovarian cancers, are likely to be susceptible to PARP inhibitors and other synthetic lethal therapies. Also disclosed herein is a STAT3-11 gene signature that can predict which cancers are likely to respond to therapy with PARP inhibitors and other synthetic lethal therapies.

Therefore, disclosed herein is a method for determining sensitivity of a cancer to synthetic lethal therapy that involves assaying a sample from the subject for gene expression of at least 1, 2, 3, 4, 5, 6, 7, 8, 9, 10, or 11 genes selected from the group consisting of SMARCAD1, PRKX, ZBTB40, ATXN2L, MDM4, AP4B1, RBM33, ATP5G2, BLMH, GPR75. ASB3, and ASPHD2, wherein elevated gene expression of at least 3, 4, 5, 6, 7, 8, 9, 10, or 11 genes selected from the group consisting of SMARCAD1, PRKX, ZBTB40, ATXN2L, MDM4, AP4B1, RBM33, ATP5G2, BLMH, GPR75. ASB3, and ASPHD2, is an indication that the cancer is sensitive to a synthetic lethal therapy.

In some embodiments, the synthetic lethal therapy is any form of synthetic lethal therapies that target any non-HR type of DNA repair. In some embodiments, the synthetic lethal therapy is a PARP inhibitor.

Also disclosed is a method for treating cancer in a subject that involves detecting in a sample from the subject elevated gene expression of at least 3, 4, 5, 6, 7, 8, 9, 10, or 11 genes selected from the group consisting of SMARCAD1, PRKX, ZBTB40, ATXN2L, MDM4, AP4B1, RBM33, ATP5G2, BLMH, GPR75. ASB3, and ASPHD2; and treating the subject with a synthetic lethal therapy.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 1A and 1B show primary B lymphocytes from healthy subjects and patients with Job's syndrome infected with EBV and placed in culture for 4 days. Representative immunofluorescence images of nuclei stained with DAPI and for EBNA2 and costained for RAD51 are shown in FIG. 1A. Aggregate data from 100 $EBNA2^{+}$ nuclei each from healthy and Job's cells are shown in FIG. 1B. Table in FIG. 10 shows percent infected cells in S phase on day 4, as determined by flow cytometry. FIGS. 1D and 1E show two healthy subject-derived EBV-transformed cell lines (LCL) transfected with siRNA to STAT3 or scrambled (Sc) siRNA and harvested 36 h later. Aggregate data from immunofluorescence images of >100 nuclei stained with DAPI and costained for ATR or RAD51 are shown in FIG. 1D. Cells were subjected to immunoblotting for STAT3 and β-actin in FIG. 1E. FIGS. 1F and 1G show bleomycin-treated LCL derived from 3 healthy subjects and 3 Job's syndrome patients enumerated for live cells on indicated days and percent recovery calculated in FIG. 1F.

Figure 1B:
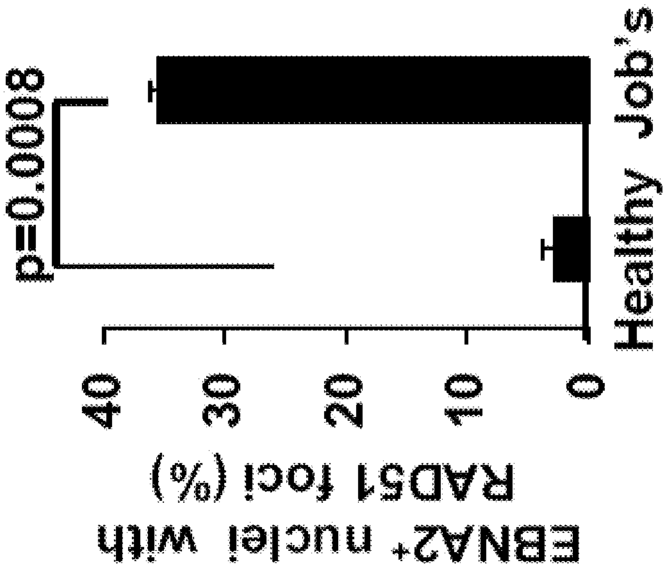
FIGS. 1A to 1G show oncovirus-infected proliferating cells with functional STAT3 demonstrate scarce RAD51 foci-containing nuclei.
Figure 1A:
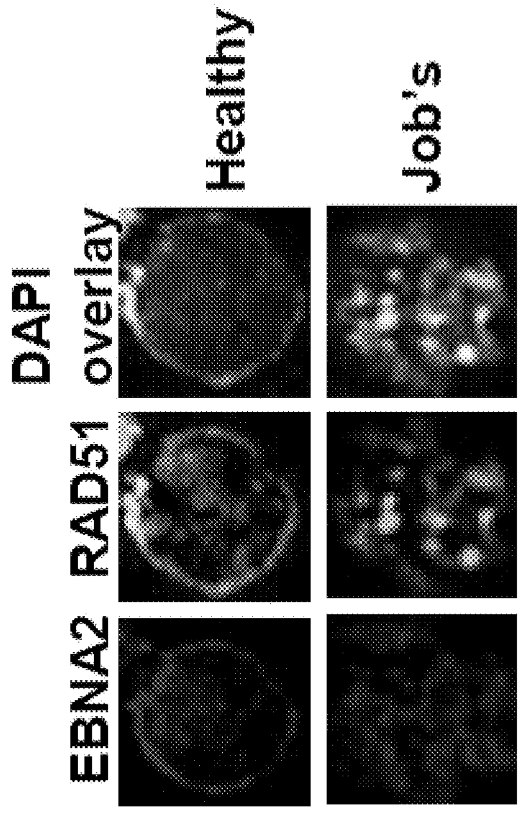
Figures 1C, 1D:
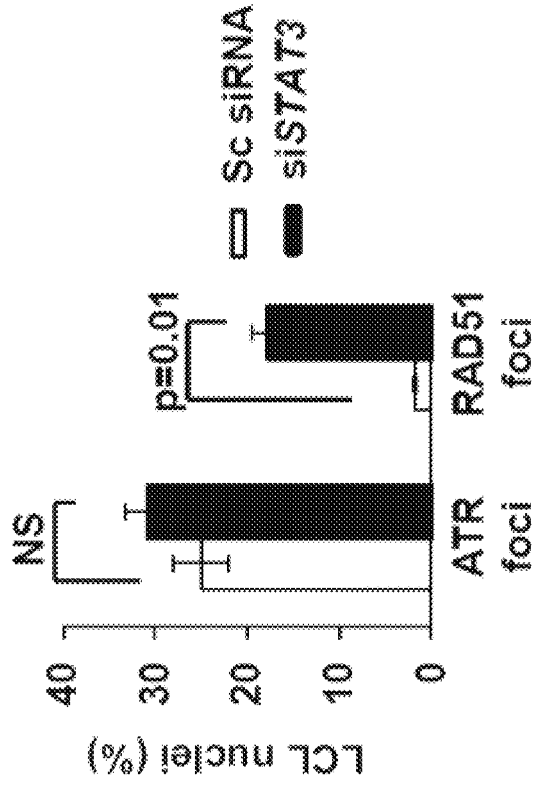
Figure 1E:
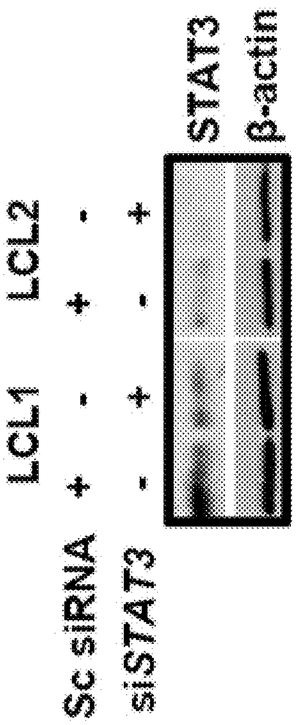
Figure 1F:
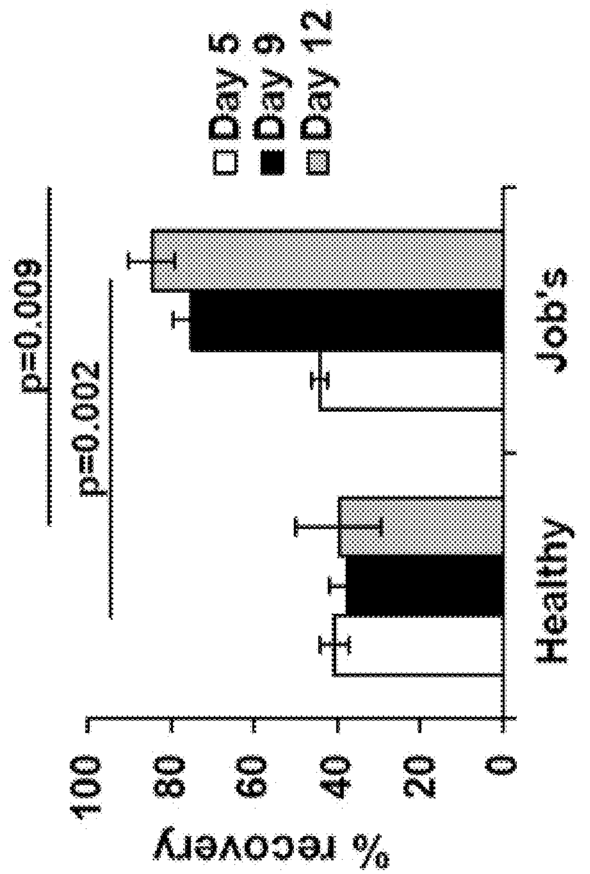
Figure 1G:
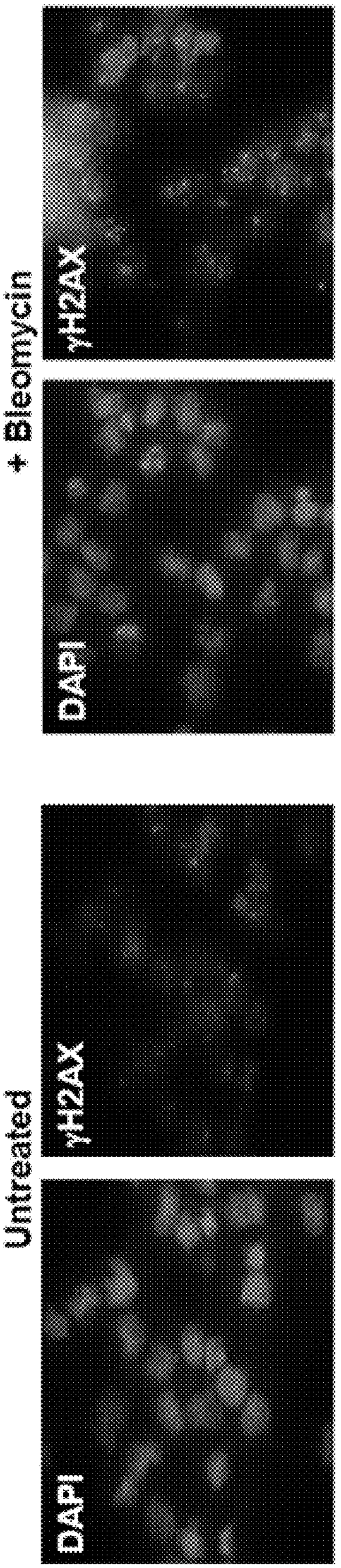

Immunofluorescence images of nuclei costained for DAPI and γH2AX are shown in FIG. 1G; error bars indicate SEM in FIGS. 1B, 1D, and 1F. Job's syndrome is an autosomal dominant hyper-IgE syndrome caused by dominant negative mutations in STAT3.

Figure 2A:
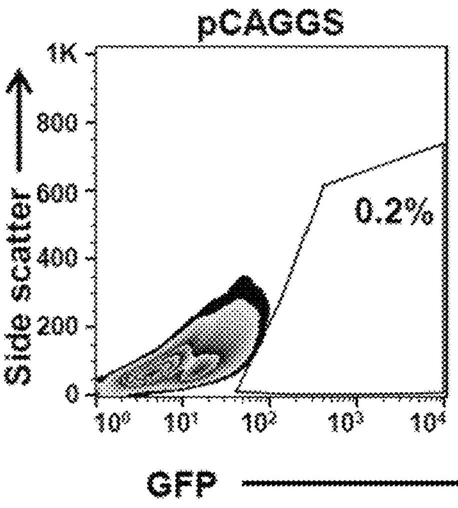
Figure 2B:
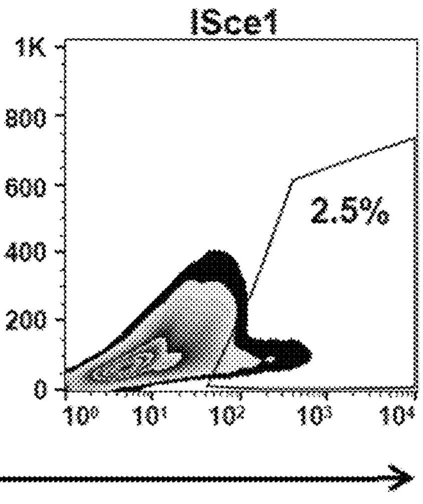
Figure 2C:
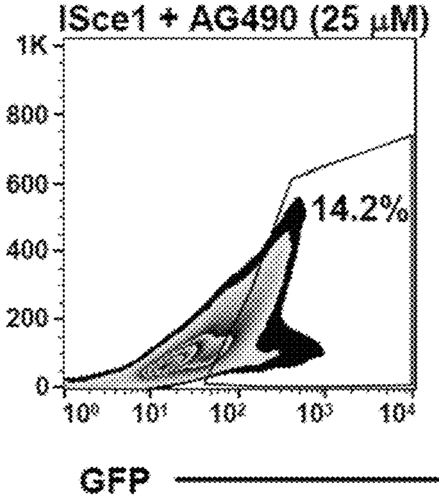
Figure 2D:
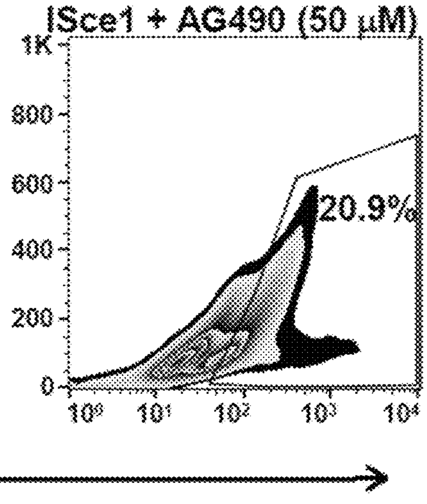
Figure 2E:
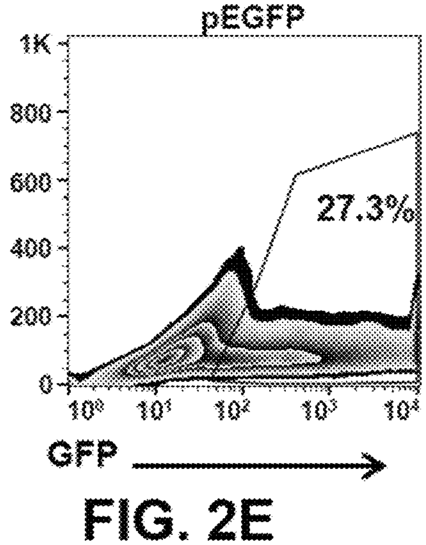
Figure 2F:
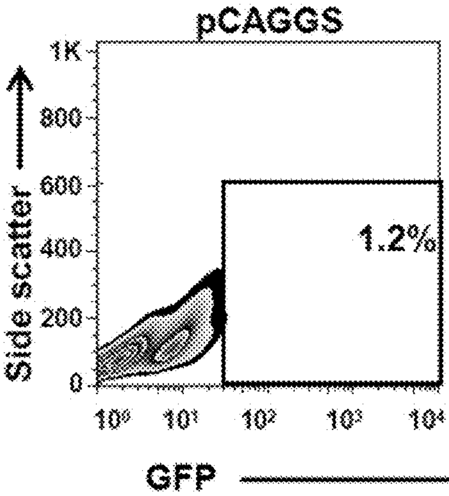
Figure 2G:
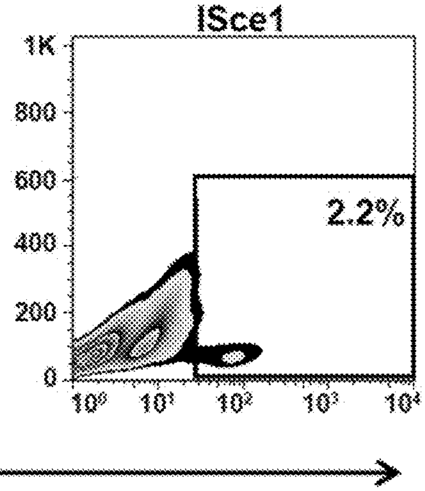
Figure 2H:
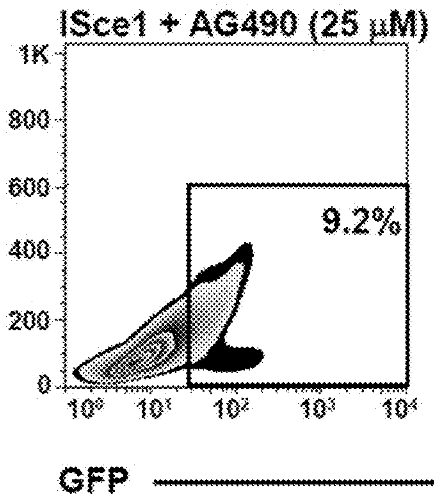
Figure 2I:
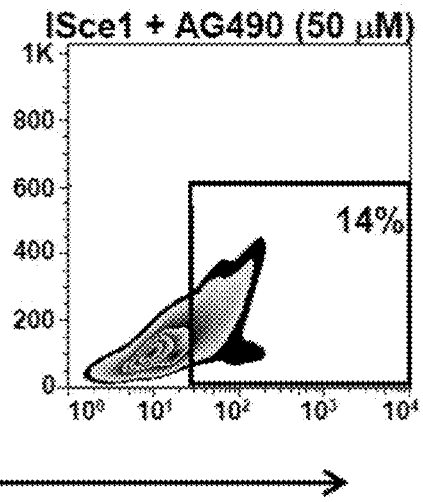
Figure 2J:
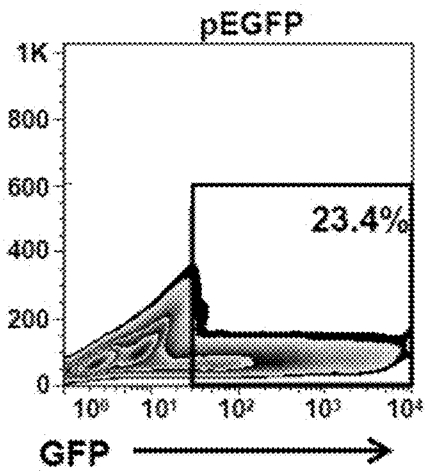

FIGS. 2A to 2O show STAT3 restricts HR repair through Chk1 in oncovirus-transformed cells. FIGS. 2A to 2K show LCL derived from a healthy subject (FIGS. 2A-2E, 2K) and EBV-positive HH514-16 Burkitt lymphoma (BL) cells (FIGS. 2F-2J, 2K) were transfected with DR-GFP plasmid (FIGS. 2A-2D, 2F-2I) and empty vector pCAGGS (FIGS. 2A, 2F) or ISce1 plasmid (FIGS. 2B-2D, 2G-2I), treated with 25 μM (FIGS. 2C, 2H) or 50 μM (FIGS. 2D, 2I) AG490 (a selective STAT3 inhibitor) after 18 h, and harvested after another 30 h for analysis of GFP-positive cells by flow cytometry (FIGS. 2A-2D, 2F-2I) and immunoblotting for phospho(p)STAT3 and β-actin (FIG. 2K). LCL (FIG. 2E) and BL cells (FIG. 2J) were transfected in parallel with pEGFP to monitor transfection efficiency. FIGS. 2L to 2O show BL cells with stably-integrated DR-GFP were transfected with Chk1 plasmid (wild-type (FIGS. 2L-2N) or S345A mutant (FIG. 2O) and pCAGGS (FIG. 2L) or ISce1 plasmid (FIGS. 2M-2O), treated with 50 μM AG490 after 18 h, and harvested after another 30 h for analysis of GFP-positive cells by flow cytometry. Numbers in plots indicate percent GFP-positive cells. Experiments were performed 3 times.

Figures 3A, 3B, 3C, 3D, 3E, 3F:
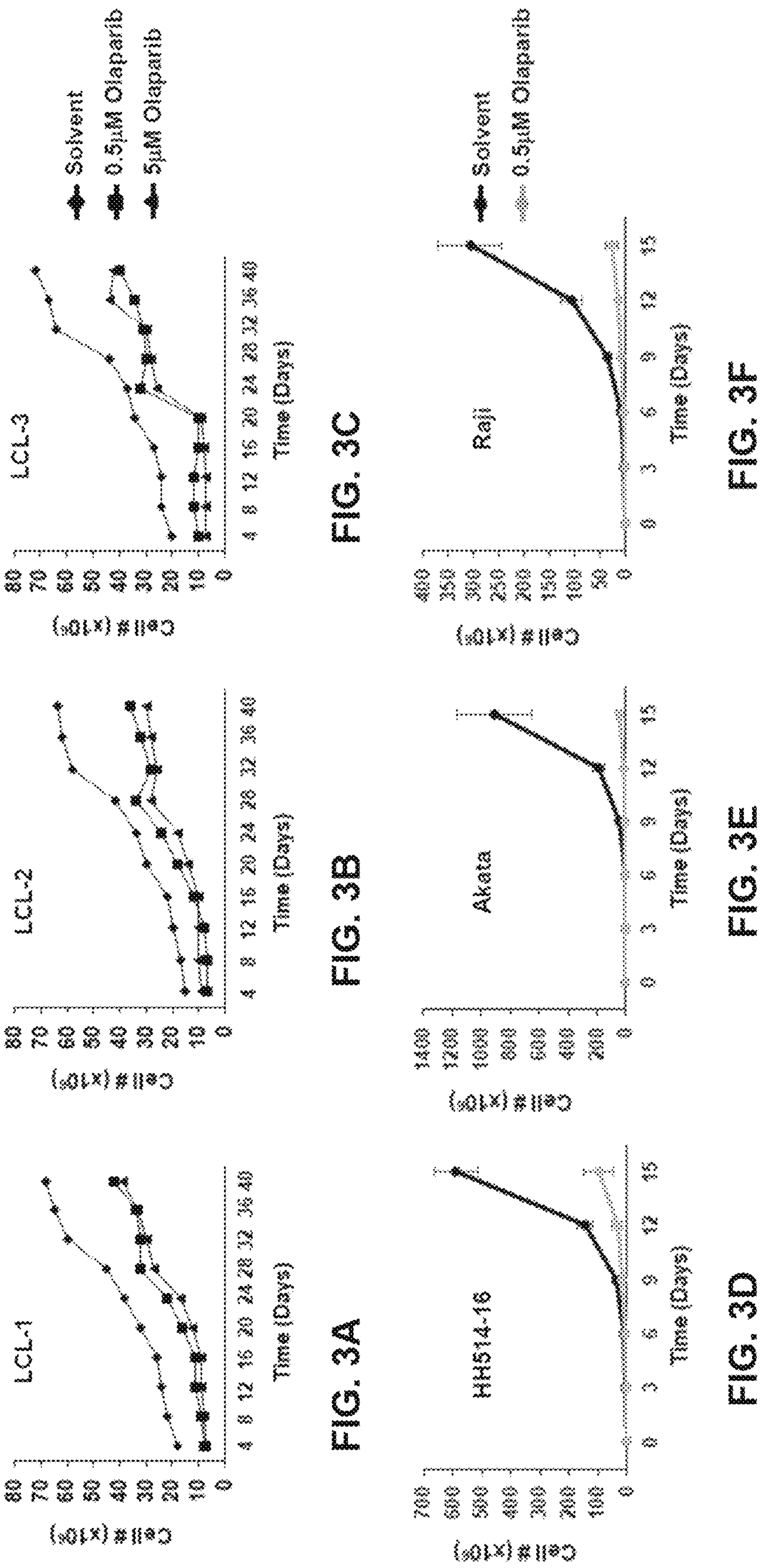

FIGS. 3A to 3N show EBV-transformed cells are susceptible to PARP inhibition and demonstrate MMEJ-mediated DSB repair. FIGS. 3A-3F show LCL derived from 3 healthy subjects (FIGS. 3A-3C) and 3 $EBV^+$ BL cell lines (HH514-16, Akata, and Raji; FIGS. 3D-3F) grown in the presence of Olaparib (added at time 0 and every 3-4 days thereafter) and enumerated for live cells on indicated days. FIGS. 3G-3N show LCL (FIGS. 3G-3J) and HH514-16 BL cells (FIGS. 3K-3N) transfected with DR-GFP plasmid (FIGS. 3G, 3H, 3K, 3L) and empty vector pCAGGS (FIGS. 3G, 3K) or ISce1 plasmid (FIGS. 3H, 3L) versus EJ2 plasmid (FIGS. 3I, 3J, 3M, 3N) and pCAGGS (FIGS. 3I, 3M) or ISce1 plasmid (FIGS. 3J, 3N) and harvested after 48 h for analysis of GFP-positive cells by flow cytometry. Numbers in plots indicate percent GFP-positive cells. Experiments were performed 3 times.

Figure 4A:
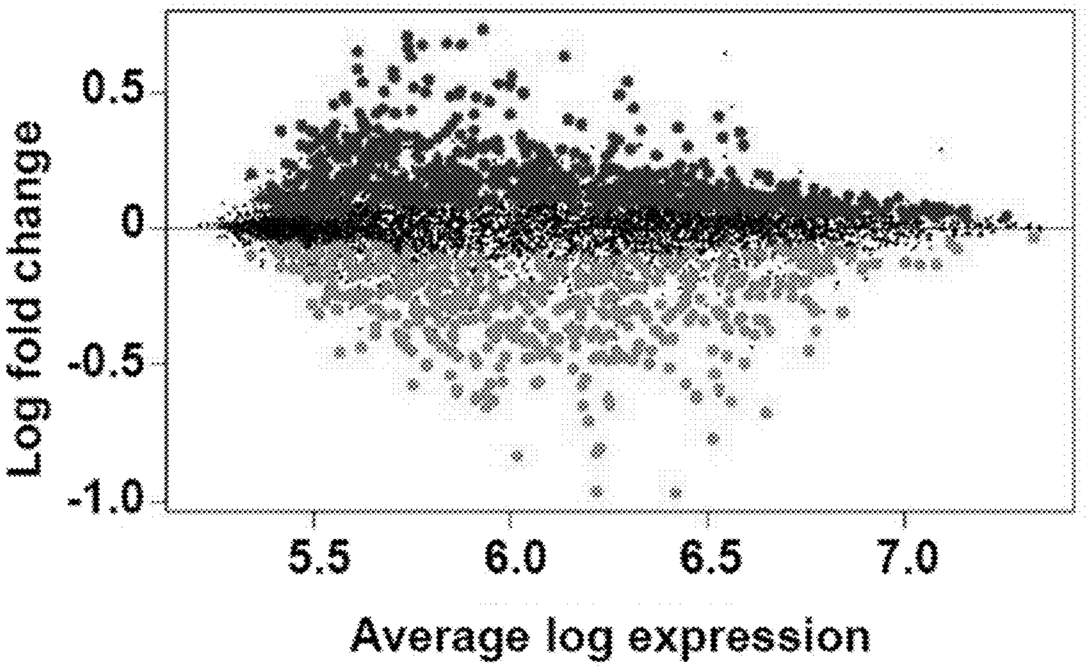
Figure 4B:
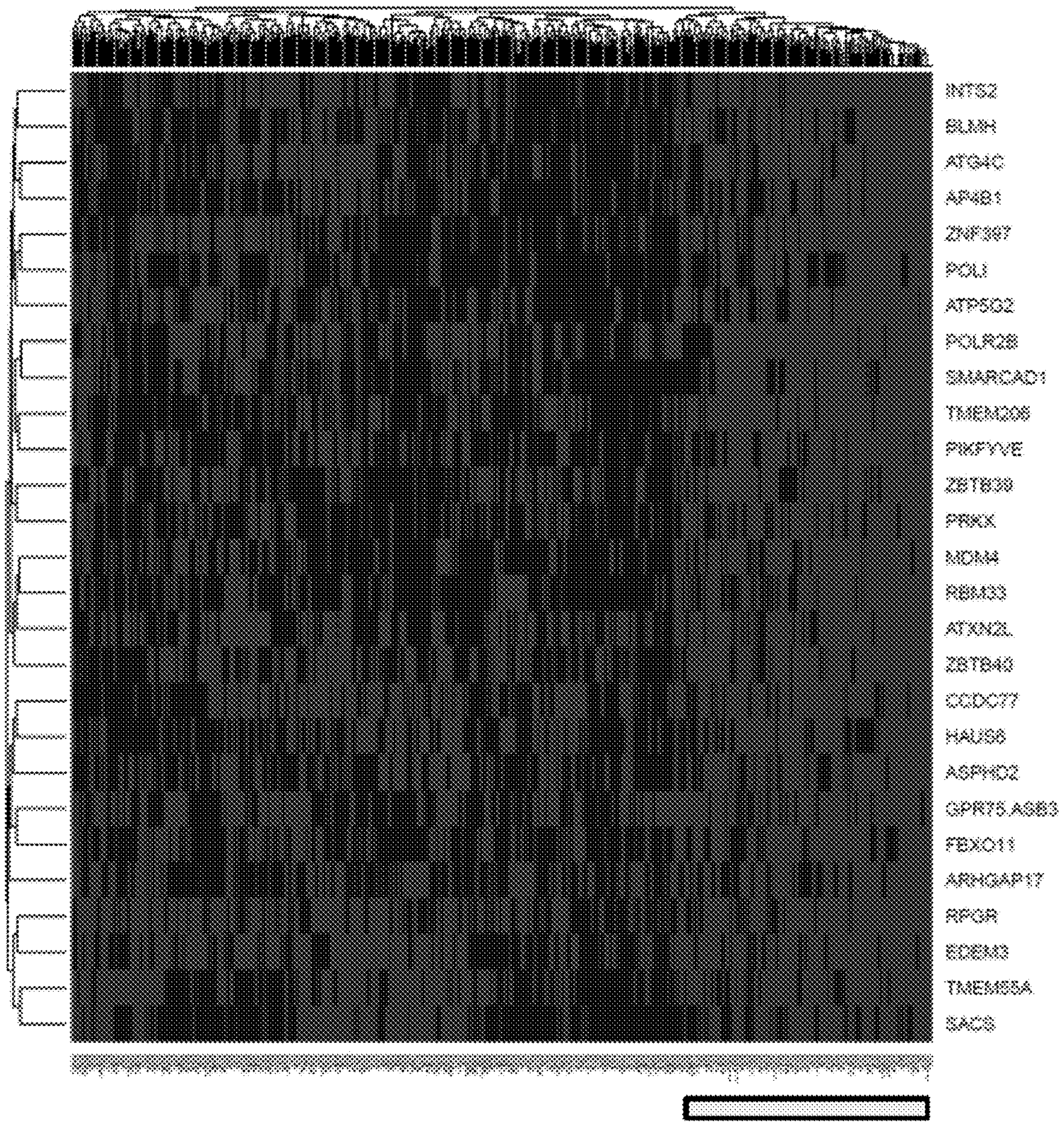
Figure 4C:
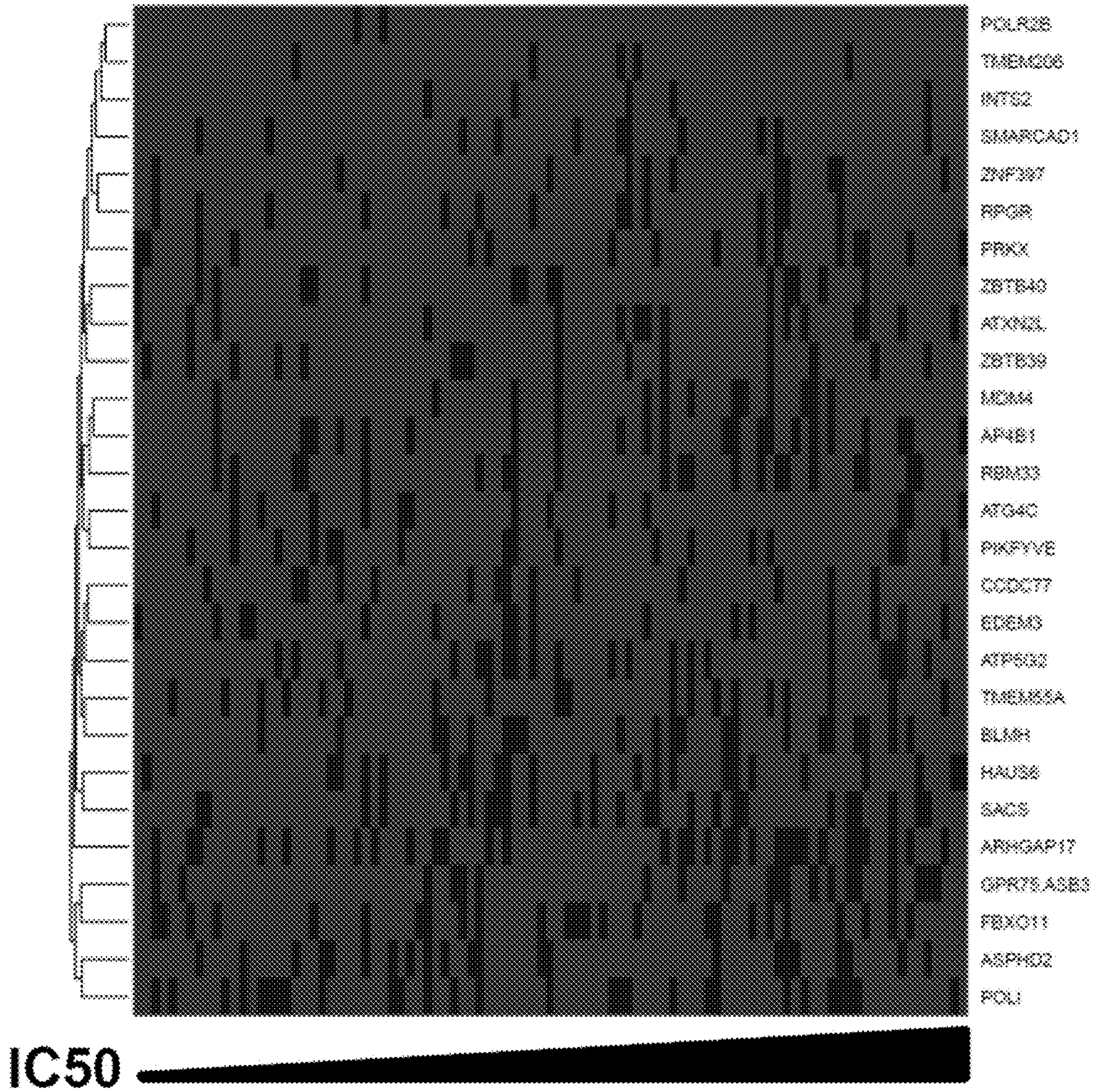
Figures 4D, 4E:
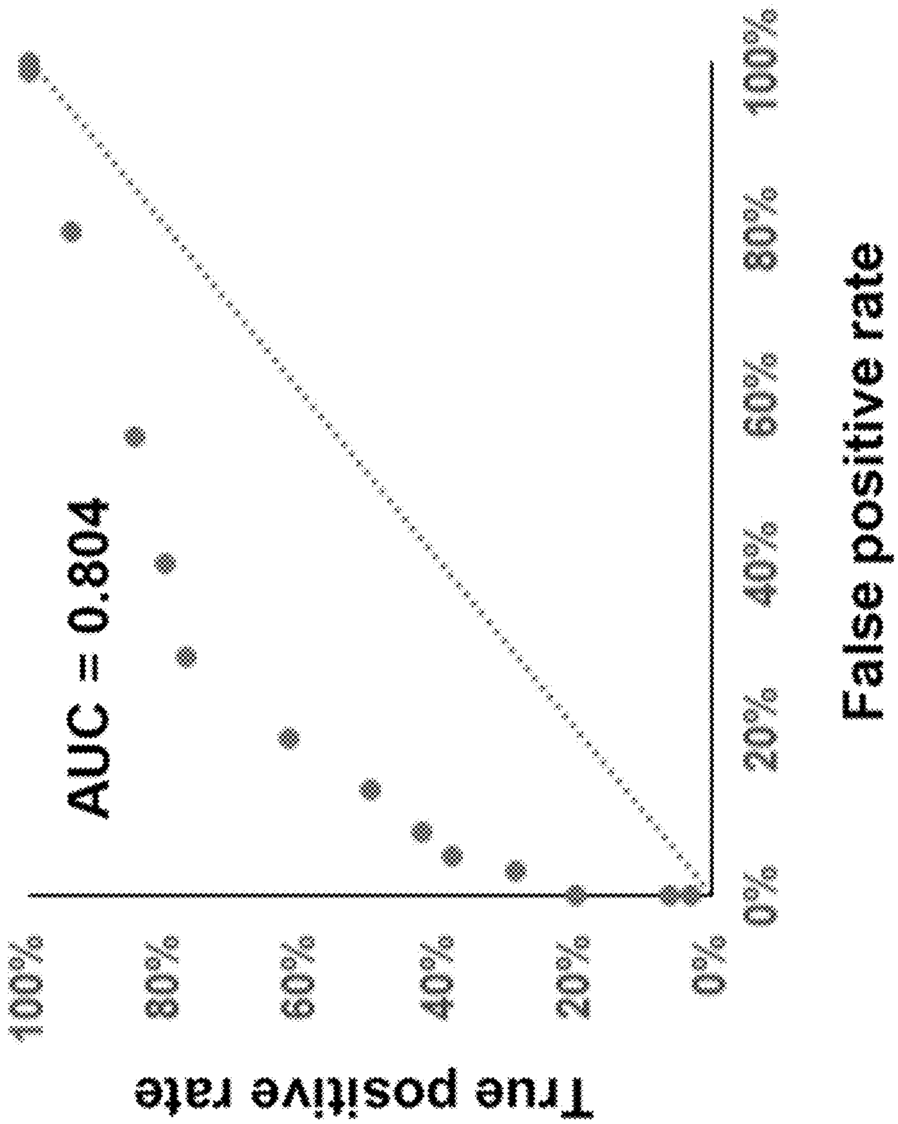

FIGS. 4A to 4E show cross-analysis between STAT3-targetome, gene expression, and PARP inhibitor sensitivity in cancer lines derived from a range of tissues. FIG. 4A is a mean-difference plot showing differential expression of STAT3 transcriptional targets between cancer lines with highest sensitivity (corresponding to ~30% of sensitive lines) and those with highest resistance (corresponding to ~10% of resistant lines) to a PARP inhibitor. Red spots represent 699 genes with significantly higher expression in highly sensitive lines, green spots correspond to 472 genes demonstrating higher expression in highly resistant lines, and black spots represent 5899 genes that were not differentially expressed. FIG. 4B is a hierarchically clustered binary plot of expression of 27 (of 699) genes with higher expression in all lines with high sensitivity to PARP inhibitor; high or low calls were based on whether expression exceeded the sensitive mean minus one standard deviation. FIG. 4C is a second binary plot, derived from the plot in FIG. 4B, displayed on an IC50 scale using the subpopulation of lines (indicated by a yellow bar in FIG. 4B) that expressed overall high levels of the 27 genes. Examination of this binary plot led to the selection of nine genes with high expression in lines with low IC50s (i.e. in sensitive lines) but low expression in lines with high IC50s (i.e. in resistant lines). Two additional genes found to be good predictors of IC50 based on independent Lasso and Elastic net analyses of STAT3-transcriptional targets were also among the 27 genes from above. These were added to the nine genes to yield an 11-gene signature (FIG. 4D). ROC curve generated using all cancer lines (>450 from a variety of tissue types) with experimental data on susceptibility to PARP inhibitor within the Cancer Genome Project dataset and the STAT3 11-gene signature (using a 60% threshold) showed an AUC of 0.804 (FIG. 4E).

Figure 5A:
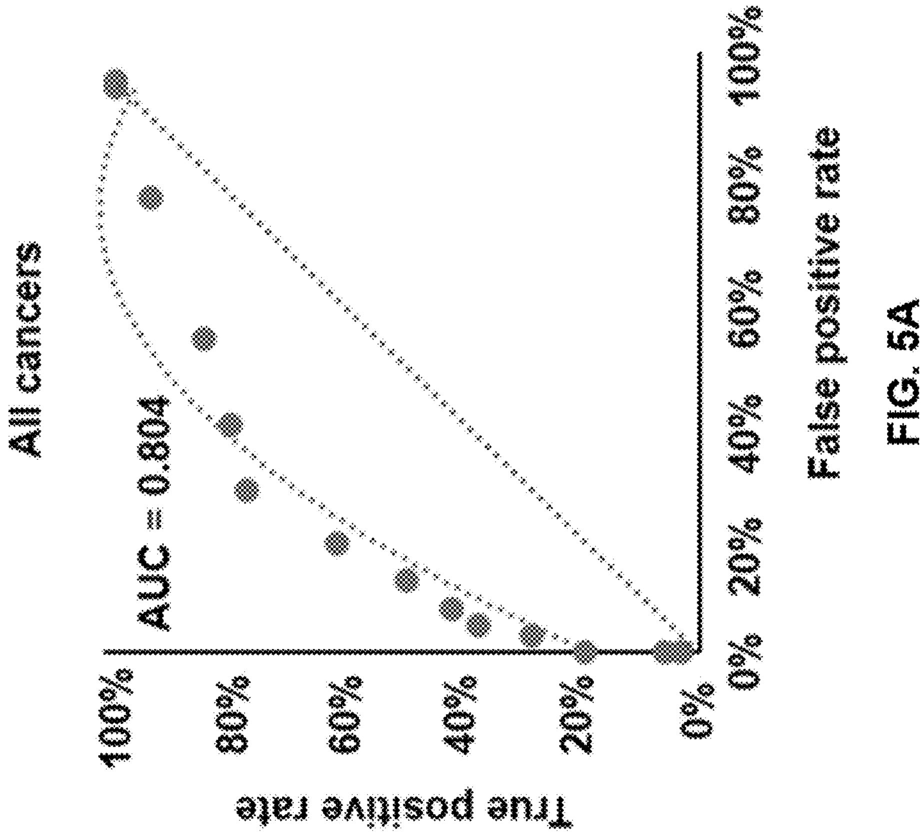
Figure 5B:
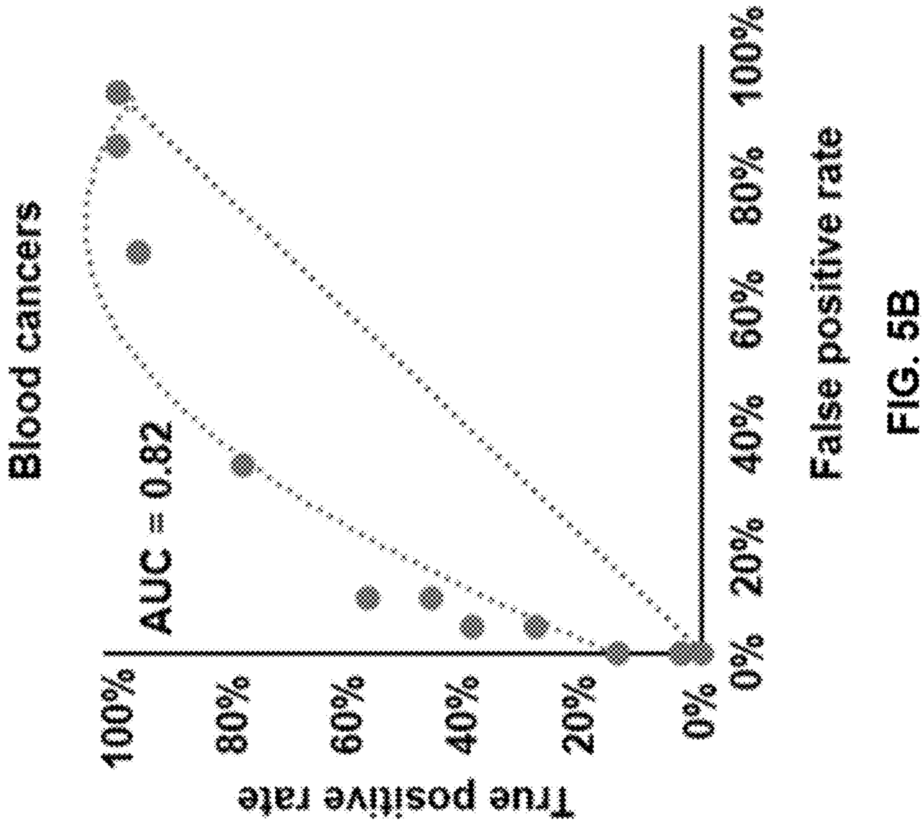
Figure 5C:
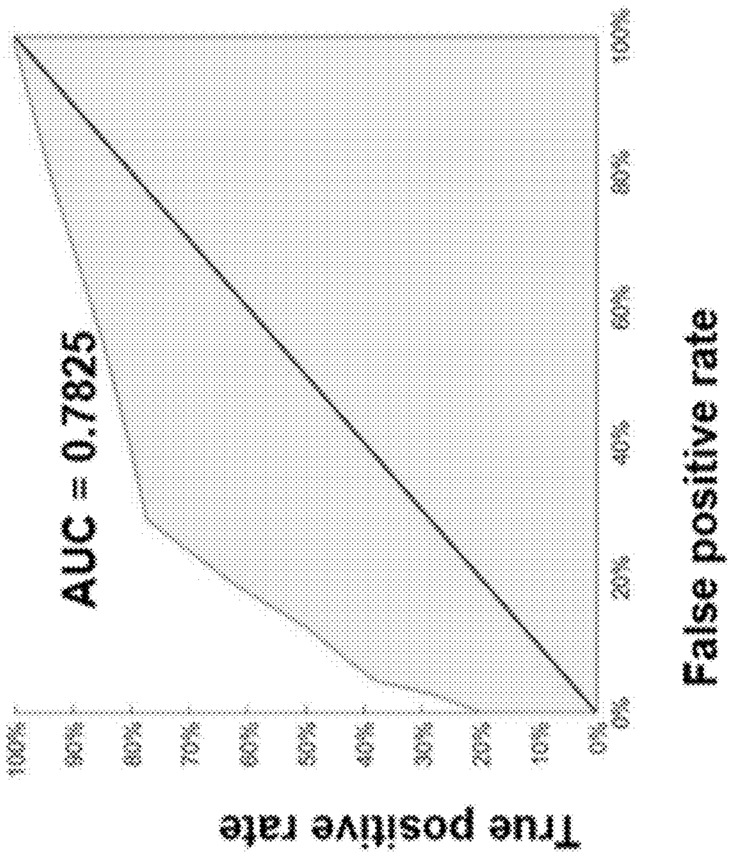

FIGS. 5A to 5C show ROC curve analysis of STAT3 11 gene set on predicting susceptibility to PARP inhibition in all cancers versus blood cancers.

Figure 6:
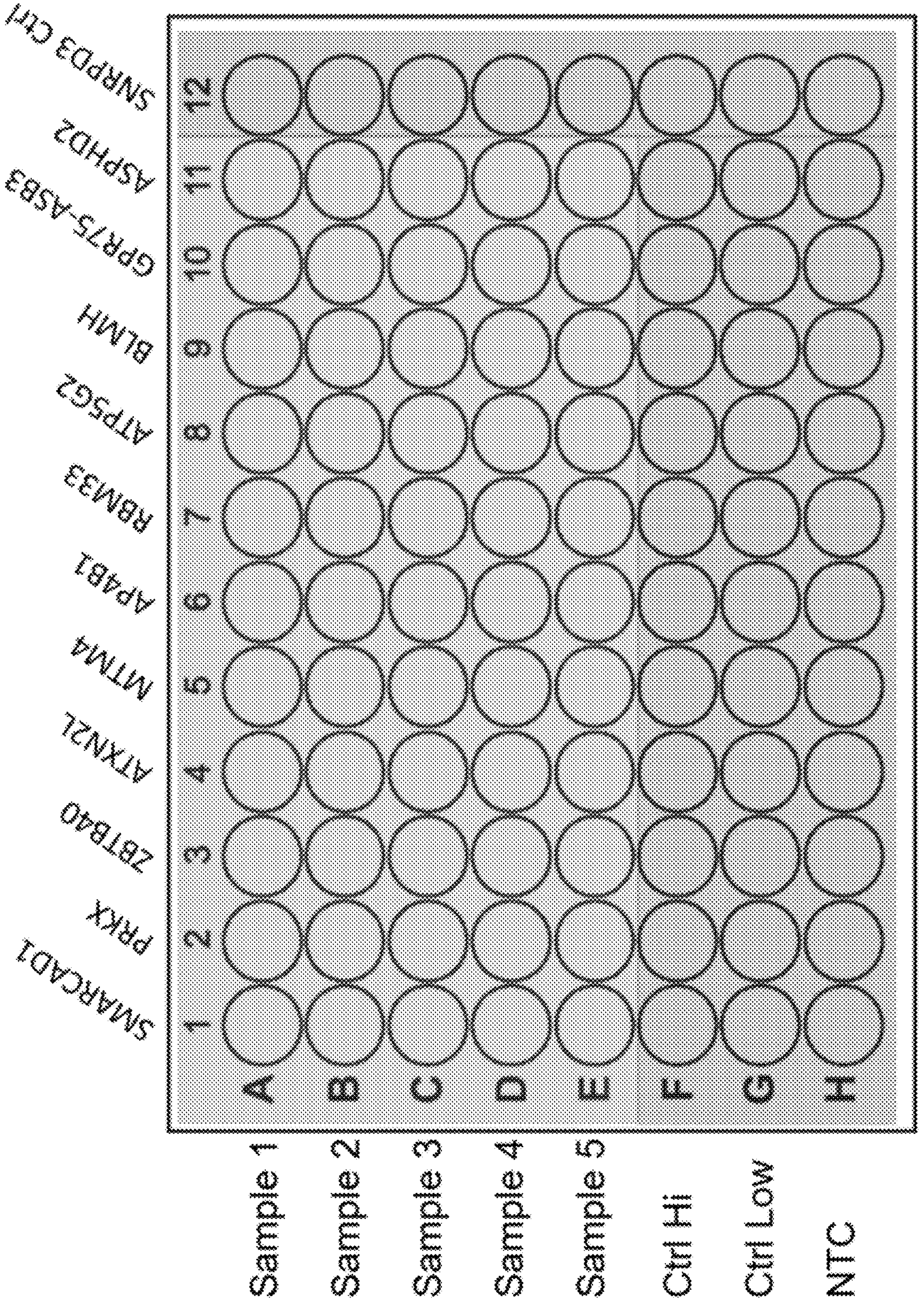

FIG. 6 shows an example 96 well plate design for an RT-qPCR assay for gene expression of each member of an 11 gene signature set, which can be compared relative to an invariant expressing housekeeping gene, such as SNRPD3 (last column of the plate), as well as compared to control cDNA derived from known cell lines that are susceptible to the synthetic lethal PARP inhibitor, Olaparib (Ctrl Hi) and resistant to Olaparib (Ctrl Low). A no template control for each individual RT-qPCR reaction is also provided for in the last row of the plate.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biology, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in °C, and pressure is at or near atmospheric. Standard temperature and pressure are defined as 20 °C and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

STAT3-11 Gene Signature

Disclosed herein is a method that involves detecting in a sample from the subject the STAT3-11 gene signature disclosed herein.

The STAT3-11 gene signature can in some embodiments, involve elevated gene expression of at least 1, 2 3, 4, 5, 6, 7, 8, 9, 10, or 11 genes selected from the group consisting of SMARCAD1, PRKX, ZBTB40, ATXN2L, MDM4, AP4B1, RBM33, ATP5G2, BLMH, GPR75, ASB3, and ASPHD2.

Methods for determining whether gene expression in a microarray is elevated are known in the art. For example, in some embodiments, the method involves normalization using a standard approach called RMA. Gene expression can be considered elevated if the level of expression exceeds 1 standard deviation below the mean for that gene in cancers found to be susceptible to a given synthetic-lethal approach. In some embodiments, gene expression is measured relative to a housekeeping gene such as beta actin (ACTB) or small nuclear ribonucleoprotein D3 (SNRPD3).

Methods of "determining gene expression levels" include methods that quantify levels of gene transcripts as well as methods that determine whether a gene of interest is expressed at all. A measured expression level may be expressed as any quantitative value, for example, a fold-change in expression, up or down, relative to a control gene or relative to the same gene in another sample, or a log ratio of expression, or any visual representation thereof, such as, for example, a "heatmap" where a color intensity is representative of the amount of gene expression detected. Exemplary methods for detecting the level of expression of a gene include, but are not limited to, Northern blotting, dot or slot blots, reporter gene matrix, nuclease protection, RT-PCR, real-time (quantitative) RT-qPCR, microarray profiling, differential display, 2D gel electrophoresis, SELDI-TOF, ICAT, enzyme assay, antibody assay, enzyme-linked immunosorbent assay (ELISA), Western blot, MNAzyme-based detection methods, and quantitative RNA-sequencing. Optionally, a gene whose level of expression is to be detected may have its RNA or complementary DNA (cDNA) amplified, for example by methods that may include one or more of: polymerase chain reaction (PCR), strand displacement amplification (SDA), loop-mediated isothermal amplification (LAMP), rolling circle amplification (RCA), recombinase polymerase amplification (RPA), transcription-mediated amplification (TMA), self-sustained sequence replication (3SR), nucleic acid sequence based amplification (NASBA), or reverse transcription polymerase chain reaction (RT-PCR).

A number of suitable high throughput formats exist for evaluating expression patterns and profiles of the disclosed genes. Multiplexing of biological marker assays listed above either by combining fluorescent reporters in a single reaction vessel or by arraying assays in a microtiter plate, chip, or bead format are common methods for assessing expression of multiple gene signatures. This can take the form of arraying individual gene expression assays (RT-qPCR or similar) along with a separate gene expression assay for an invariantly expressed endogenous gene such as NEDD8, SNRPD3, GAPDH, 18S rRNA, or similar. Expression levels may be compared using a variety of statistical methods such as the ΔΔCq analysis method. Likewise, the 11 gene signatures may be incorporated into a gene expression DNA macro or microarray format including a number of invariantly expressed endogenous genes as references for making determinations of high and low gene expression levels for members of the disclosed 11 gene signature.

An example 96 well plate design for such a RT-qPCR assay is illustrated in FIG. 6 with Taqman primer and probe designs shown in Table 1. In such a layout, gene expression for each member of the 11 gene signature set may be compared relative to an invariant expressing housekeeping gene, such as SNRPD3 (last column of the plate), as well as compared to control cDNA derived from known cell lines that are susceptible to the synthetic lethal PARP inhibitor, Olaparib (Ctrl Hi) and resistant to Olaparib (Ctrl Low). A no template control for each individual RT-qPCR reaction is also provided for in the last row of the plate (FIG. 6).

TABLE 1

Taqman RT-qPCR primer designs for the 11 gene signature to predict susceptibility of cancers to synthetic-lethal therapies.

| Gene | Sequence Locus / RT-qPCR Signatures |
|---|---|
| SMARCAD1 | NC_000004.12 Chr. 4 (94207608 . . . 94291292)<br>GTGATTATAGTTTCTGAGCCATCTG (SEQ ID NO: 1)<br>CCAATTCCGAAAGGTCTTCCAG (SEQ ID NO: 2)<br>FAM-AAGAGTCCCAAGGCCTTCCTACCATG-BHQ2 (SEQ ID NO: 3) |

TABLE 1-continued

Taqman RT-qPCR primer designs for the 11 gene signature to predict susceptibility of cancers to synthetic-lethal therapies.

| Gene | Sequence Locus / RT-qPCR Signatures |
|---|---|
| PRKX | NC_000023.11 Chr. X (3604340 . . . 3713649, complement)<br>GCGATTAGGAAACATGAAGAACGG (SEQ ID NO: 4)<br>CTTGGGCACGATGGGAGCTT (SEQ ID NO: 5)<br>FAM-TCCGCTCCGTGGACTGGGAAGCT-BHQ2 (SEQ ID NO: 6) |
| ZBTB40 | NC_000001.11 Chr. 1 (22428838 . . . 22531157)<br>TCAGTCCCGGCCATTGAAATAT (SEQ ID NO: 7)<br>CCTTAGTAAGGACACCAATGTATG (SEQ ID NO :8)<br>FAM-CATCAGTCCCGGCCATTGAAATATGTTT-BHQ2 (SEQ ID NO :9) |
| ATXN2L | NC_000016.10 Chr. 16 (28823048 . . . 28837237)<br>CGGCCTGGCCTTAGCTCTTT (SEQ ID NO: 10)<br>ATGCGGGAAGGGCCTCCAT (SEQ ID NO: 11)<br>FAM-CACCTCGTGGCCCTCACCATCTG-BHQ2 (SEQ ID NO: 12) |
| MDM4 | NC_000001.11 Chr. 1 (204516377 . . . 204558120)<br>GAAATGTTCACTGTTAAAGAGGTCAT (SEQ ID NO: 13)<br>GCATATCATAGAGAGGGCTTGG (SEQ ID NO: 14)<br>FAM-TCTTTCACGGAGAAGCTCTGACGTCC-BHQ2 (SEQ ID NO: 15) |
| AP4B1 | NC_000001.11 Chr. 1 (113894194 . . . 113905067, complement)<br>GAATGTGCAGCAGGTGCTAG (SEQ ID NO: 16)<br>CATAGGTGGCATTGCCAGGA (SEQ ID NO: 17)<br>FAM-AGCTTCGAGGGTACTGCACGGATGT-BHQ2 (SEQ ID NO: 18) |
| RBM33 | NC_000007.14 Ch. 7 (155644494 . . . 155781485)<br>ACTTGGAGAAGATTTGCTATCTGG (SEQ ID NO: 19)<br>GTAACACCCTGAGAACTGAAATTTT (SEQ ID NO: 20)<br>FAM-ATCAGTCGGATTTGTCAGATGAAGAGC-BHQ2 (SEQ ID NO: 21) |
| ATP5G2 | NC_000012.12 Chr. 12 (53665160 . . . 53677546, complement)<br>CCACTCCCTCCTTGGTCAAG (SEQ ID NO: 22)<br>CCAAGCTGCTGAGGCTCTC (SEQ ID NO: 23)<br>FAM-TGTCAGTATCTCCGGTCGTTTCAGC-BHQ2 (SEQ ID NO: 24) |
| BLMH | NC_000017.11 Chr. 17 (30248203 . . . 30291944, complement)<br>AGCTCAGGGCGATGCTGGA (SEQ ID NO: 25)<br>TAACAGCGTTCAACCTTGTCCC (SEQ ID NO: 26)<br>FAM-CTTGTCTGAATGTTATGAGGCTTCCATT-BHQ2 (SEQ ID NO: 27) |
| GPR75-ASB3 | NC_000002.12 Chr. 2 (53670293 . . . 53860033, complement)<br>CGATGATGCCTCTAGTCCTG (SEQ ID NO: 28)<br>CATTTGTTTGACCAGTCTGCCG (SEQ ID NO: 29)<br>FAM-TCATCCAGAGCGGCAGGCGGA-BHQ2 (SEQ ID NO: 30) |
| ASPHD2 | NC_000022.11 Chr. 22 (26429260 . . . 26445015)<br>ATCCGATGCCATTTAGGTCTGAA (SEQ ID NO: 31)<br>CCATCCTCTGCTGAACCTTC (SEQ ID NO: 32)<br>FAM-CTCCAAATGGCTGTGAGCTGGTG-BHQ2 (SEQ ID NO: 33) |
| SNRPD3 Control | NC_000022.11 Chr. 22 (24555650 . . . 24574971)<br>GGCACAGCTGGAGCAGGTAT (SEQ ID NO: 34)<br>CTTCAGCATGTCAGGCAAAATC (SEQ ID NO: 35)<br>FAM-ATCCGTGGCAGCAAAATCCGCTTT-BHQ2 (SEQ ID NO: 36) |

The housekeeping gene SNRPD3 represents an endogenous expression control with which to compare expression levels of the individual members of the 11 gene signature set.

Numerous technological platforms for performing high throughput expression analysis are known. Generally, such methods involve a logical or physical array of either the subject samples, the biomarkers, or both. Common array formats include both liquid and solid phase arrays. For example, assays employing liquid phase arrays, e.g., for hybridization of nucleic acids, binding of antibodies or other receptors to ligand, etc., can be performed in multiwell or microtiter plates. Microtiter plates with 96, 384 or 1536 wells are widely available, and even higher numbers of wells, e.g., 3456 and 9600 can be used. In general, the choice of microtiter plates is determined by the methods and equipment, e.g., robotic handling and loading systems, used for sample preparation and analysis. Exemplary systems include, e.g., xMAP® technology from Luminex (Austin, TX), the SECTOR® Imager with MULTI-ARRAY® and MULTI-SPOT® technologies from Meso Scale Discovery (Gaithersburg, MD), the ORCA™ system from Beckman-Coulter, Inc. (Fullerton, Calif.) and the ZYMATE™ systems from Zymark Corporation (Hopkinton, MA), miRCURY LNA™ microRNA Arrays (Exiqon, Woburn, MA).

Alternatively, a variety of solid phase arrays can favorably be employed to determine expression patterns in the context of the disclosed methods, assays and kits. Exemplary formats include membrane or filter arrays (e.g., nitrocellulose, nylon), pin arrays, and bead arrays (e.g., in a liquid "slurry"). Typically, probes corresponding to nucleic acid or protein reagents that specifically interact with (e.g., hybridize to or bind to) an expression product corresponding to a member of the candidate library, are immobilized, for example by direct or indirect cross-linking, to the solid support. Essentially any solid support capable of withstanding the reagents and conditions necessary for performing the particular expression assay can be utilized. For example, functionalized glass, silicon, silicon dioxide, modified silicon, any of a variety of polymers, such as (poly)tetrafluoroethylene, (poly)vinylidenedifluoride, polystyrene, polycarbonate, or combinations thereof can all serve as the substrate for a solid phase array.

In one embodiment, the array is a "chip" composed, e.g., of one of the above-specified materials. Polynucleotide probes, e.g., RNA or DNA, such as cDNA, synthetic oligonucleotides, and the like, or binding proteins such as antibodies or antigen-binding fragments or derivatives thereof, that specifically interact with expression products of individual components of the candidate library are affixed to the chip in a logically ordered manner, i.e., in an array. In addition, any molecule with a specific affinity for either the sense or anti-sense sequence of the marker nucleotide sequence (depending on the design of the sample labeling), can be fixed to the array surface without loss of specific affinity for the marker and can be obtained and produced for array production, for example, proteins that specifically recognize the specific nucleic acid sequence of the marker, ribozymes, peptide nucleic acids (PNA), or other chemicals or molecules with specific affinity.

Microarray expression may be detected by scanning the microarray with a variety of laser or CCD-based scanners, and extracting features with numerous software packages, for example, IMAGENE™ (Biodiscovery), Feature Extraction Software (Agilent), SCANLYZE™ (Stanford Univ., Stanford, CA), GENEPIX™ (Axon Instruments).

An array is an orderly arrangement of samples, providing a medium for matching known and unknown DNA samples based on base-pairing rules and automating the process of identifying the unknowns. An array experiment can make use of common assay systems such as microplates or standard blotting membranes, and can be created by hand or make use of robotics to deposit the sample. In general, arrays are described as macroarrays or microarrays, the difference being the size of the sample spots.

Macroarrays contain sample spot sizes of about 300 microns or larger and can be easily imaged by existing gel and blot scanners. The sample spot sizes in microarray can be 300 microns or less, but typically less than 200 microns in diameter and these arrays usually contains thousands of spots. Microarrays require specialized robotics and/or imaging equipment that generally are not commercially available as a complete system. Terminologies that have been used in the literature to describe this technology include, but not limited to: biochip, DNA chip, DNA microarray, GeneChip® (Affymetrix, Inc which refers to its high density, oligonucleotide-based DNA arrays), and gene array.

A DNA microarray is a collection of microscopic DNA spots attached to a solid surface, such as glass, plastic or silicon chip forming an array for the purpose of expression profiling, monitoring expression levels for thousands of genes simultaneously. DNA microarrays, or DNA chips are fabricated by high-speed robotics, generally on glass or nylon substrates, for which probes with known identity are used to determine complementary binding, thus allowing massively parallel gene expression and gene discovery studies. An experiment with a single DNA chip can provide information on thousands of genes simultaneously. It is herein contemplated that the disclosed microarrays can be used to monitor gene expression, disease diagnosis, gene discovery, drug discovery (pharmacogenomics), and toxicological research or toxicogenomics.

The affixed DNA segments are generally known as probes, thousands of which can be placed in known locations on a single DNA microarray. Microarray technology evolved from Southern blotting, whereby fragmented DNA is attached to a substrate and then probed with a known gene or fragment. Measuring gene expression using microarrays is relevant to many areas of biology and medicine, such as studying treatments, disease, and developmental stages. For example, microarrays can be used to identify disease genes by comparing gene expression in diseased and normal cells.

There are two variants of the DNA microarray technology, in terms of the property of arrayed DNA sequence with known identity. Type I microarrays comprise a probe cDNA (500~5,000 bases long) that is immobilized to a solid surface such as glass using robot spotting and exposed to a set of targets either separately or in a mixture. This method is traditionally referred to as DNA microarray. With Type I microarrays, localized multiple copies of one or more polynucleotide sequences, preferably copies of a single polynucleotide sequence are immobilized on a plurality of defined regions of the substrate's surface. A polynucleotide refers to a chain of nucleotides ranging from 5 to 10,000 nucleotides. These immobilized copies of a polynucleotide sequence are suitable for use as probes in hybridization experiments.

Type II microarrays comprise an array of oligonucleotides (20~80-mer oligos) or peptide nucleic acid (PNA) probes that is synthesized either in situ (on-chip) or by conventional synthesis followed by on-chip immobilization. The array is exposed to labeled sample DNA, hybridized, and the identity/abundance of complementary sequences are determined. This method, "historically" called DNA chips, was developed at Affymetrix, Inc., which sells its photolithographically fabricated products under the GeneChip® trademark.

The basic concept behind the use of Type II arrays for gene expression is simple: labeled cDNA or cRNA targets derived from the mRNA of an experimental sample are hybridized to nucleic acid probes attached to the solid support. By monitoring the amount of label associated with each DNA location, it is possible to infer the abundance of each mRNA species represented. Although hybridization has been used for decades to detect and quantify nucleic acids, the combination of the miniaturization of the technology and the large and growing amounts of sequence information, have enormously expanded the scale at which gene expression can be studied.

In spotted microarrays (or two-channel or two-colour microarrays), the probes are oligonucleotides, cDNA or small fragments of PCR products corresponding to mRNAs. This type of array is typically hybridized with cDNA from two samples to be compared (e.g., patient and control) that are labeled with two different fluorophores. The samples can be mixed and hybridized to one single microarray that is then scanned, allowing the visualization of up-regulated and down-regulated genes in one go. The downside of this is that the absolute levels of gene expression cannot be observed, but only one chip is needed per experiment. One example of a provider for such microarrays is Eppendorf with their DualChip® platform.

In oligonucleotide microarrays (or single-channel microarrays), the probes are designed to match parts of the sequence of known or predicted mRNAs. There are commercially available designs that cover complete genomes from companies such as GE Healthcare, Affymetrix, Ocimum Biosolutions, or Agilent. These microarrays give estimations of gene expression and therefore the comparison of two conditions requires the use of two separate microarrays.

Long Oligonucleotide Arrays are composed of 60-mers, or 50-mers and are produced by ink-jet printing on a silica substrate. Short Oligonucleotide Arrays are composed of 25-mer or 30-mer and are produced by photolithographic synthesis (Affymetrix) on a silica substrate or piezoelectric deposition (GE Healthcare) on an acrylamide matrix. More recently, Maskless Array Synthesis from NimbleGen Systems has combined flexibility with large numbers of probes. Arrays can contain up to 390,000 spots, from a custom array design. New array formats are being developed to study specific pathways or disease states for a systems biology approach.

Oligonucleotide microarrays often contain control probes designed to hybridize with RNA spike-ins. The degree of hybridization between the spike-ins and the control probes is used to normalize the hybridization measurements for the target probes.

In another embodiment, quantitative and relative gene expression can be assessed directly from RNA or cDNA by digital PCR. In digital PCR, individual or multiplexed PCR reactions on a given sample are partitioned into many individual reactions (thousands to millions) by physical separation on a microscopic well chip, bead association, and/or emulsion. This results in limiting dilution of target molecules among the partitions. Individual partitions are assayed as positive or negative fluorometrically to directly quantify the number of target molecules in a given sample.

Synthetic Lethal Therapies

Synthetic lethality arises when a combination of deficiencies in the expression of two or more genes leads to cell death, whereas a deficiency in only one of these genes does not. The deficiencies can arise through mutations, epigenetic alterations or inhibitors of one of the genes. Synthetic lethality has utility for purposes of molecular targeted cancer therapy, with the first example of a molecular targeted therapeutic exploiting a synthetic lethal exposed by an inactivated tumor suppressor gene (BRCA1 and 2) receiving FDA approval in 2016 (PARP inhibitor). A sub-case of synthetic lethality, where vulnerabilities are exposed by the deletion of passenger genes rather than one or more tumor suppressors is the so-called “collateral lethality”. Therapies other than PARP inhibitors that may interfere with any non-HR type of DNA repair including but not limited to base excision repair, microhomology-mediated end joining, nucleotide excision repair, non-homologous end joining, and inter/intrastrand cross-link repair are expected to be therapeutic for cancers with active STAT3.

PARP Inhibitors

PARP inhibitors are a group of pharmacological inhibitors of the enzyme poly ADP ribose polymerase (PARP). They are developed for multiple indications including the treatment of cancer. Several forms of cancer are more dependent on PARP than regular cells, making PARP an attractive target for cancer therapy. PARP-1 inhibitors are particularly useful in the combination therapies described herein. PARP-1 inhibitors can be purchased from commercial vendors such as Selleck Chemicals. Examples of PARP inhibitors include Rucaparib, AG14361, Veliparib, Iniparib, Olaparib, Niraparib, talazoparib, and INO-1001.

The disclosed compositions, such as PARP inhibitors, can be used therapeutically in combination with a pharmaceutically acceptable carrier. By “pharmaceutically acceptable” is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The materials may be in solution, suspension (for example, incorporated into microparticles, liposomes, or cells). These may be targeted to a particular cell type via antibodies, receptors, or receptor ligands. Suitable carriers and their formulations are described in Remington: The Science and Practice of Pharmacy. Typically, an appropriate amount of a pharmaceutically-acceptable salt is used in the formulation to render the formulation isotonic. Examples of the pharmaceutically-acceptable carrier include, but are not limited to, saline, Ringer’s solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer’s dextrose, dextrose and sodium chloride, lactated Ringer’s, or fixed oils. Intravenous vehicles include fluid and nutrient replenishers, electrolyte replenishers (such as those based on Ringer’s dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

The herein disclosed compositions, including pharmaceutical composition, may be administered in a number of ways depending on whether local or systemic treatment is desired, and on the area to be treated. For example, the disclosed compositions can be administered intravenously, intraperitoneally, intramuscularly, subcutaneously, intracavity, or transdermally. The compositions may be administered orally, parenterally (e.g., intravenously), by intramuscular injection, by intraperitoneal injection, transdermally, extracorporeally, ophthalmically, vaginally, rectally, intranasally, topically or the like, including topical intranasal administration or administration by inhalant.

Parenteral administration of the composition, if used, is generally characterized by injection. Injectables can be prepared in conventional forms, either as liquid solutions or suspensions, solid forms suitable for solution of suspension in liquid prior to injection, or as emulsions.

The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein. For example, effective dosages and schedules for administering the compositions may be determined empirically, and making such determinations is within the skill in the art. The dosage ranges for the administration of the compositions are those large enough to produce the desired effect in which the symptoms disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., Handbook of Monoclonal Antibodies, Ferrone et al., eds., Noges Publications, Park Ridge, N.J., (1985) ch. 22 and pp. 303-357; Smith et al., Antibodies in Human Diagnosis and Therapy, Haber et al., eds., Raven Press, New York (1977) pp. 365-389. A typical daily dosage of the antibody used alone might range from about 1 μg/kg to up to 100 mg/kg of body weight or more per day, depending on the factors mentioned above.

Cancers

Cancer in the disclosed methods refers to any cell in a subject undergoing unregulated growth, invasion, or metastasis. In some aspects, the cancer can be any neoplasm or tumor for which radiotherapy, chemotherapy, hormone therapy, or immunotherapy is currently used. Alternatively, the cancer can be a neoplasm or tumor that is not sufficiently sensitive to radiotherapy or other therapies using standard methods. Thus, the cancer can be a sarcoma, lymphoma, leukemia, carcinoma, adenocarcinoma, blastoma, or germ cell tumor. A representative but non-limiting list of cancers that the disclosed compositions can be used to treat include lymphoma, B cell lymphoma, T cell lymphoma, mycosis fungoides, Burkitt lymphoma, post-transplant lymphoproliferative diseases or lymphomas, AIDS-associated malignancies, Hodgkin's Disease, myeloid leukemia, bladder cancer, brain cancer, nervous system cancer, head and neck cancer, squamous cell carcinoma of head and neck, nasopharyngeal cell carcinoma, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and virus-associated cancers and diseases (such as those linked to or caused by Epstein-Barr virus [e.g. chronic active EBV infection and EBV-related cancers such as Burkitt lymphoma, Hodgkin's disease, post-transplant or immunocompromise-associated lymphoproliferative diseases or lymphomas, AIDS-associated lymphomas, gastric carcinomas, and nasopharyngeal cell carcinoma], Kaposi's Sarcoma-Associated Herpesvirus, Human Papillomavirus, Hepatitis B virus, Human T-cell leukemia virus type 1, Merkel cell polyomavirus).

In some embodiments, the cancer comprises an ovarian or breast cancer. In particular embodiments, the cancer lacks BRCA1 or BRCA2 gene mutations.

Some of the cancers that are implicated include (but are not limited to) B cell lymphomas, Ewing's sarcoma, leukemias, breast cancer, cervical cancer, ovarian cancers, colorectal cancers, and osteosarcomas.

A number of embodiments of the invention have been described. Nevertheless, it will be understood that various modifications may be made without departing from the spirit and scope of the invention. Accordingly, other embodiments are within the scope of the following claims.

EXAMPLES

Example 1

STAT3 Imparts BRCAness by Impairing Homologous Recombination Repair in Oncovirus-Transformed Cells Results STAT3 Impairs RAD51 Foci Formation in EBV-Infected Cells.

During DNA replication, cell cycle checkpoints and DNA repair need to be tightly coordinated. Such coordination ensures that cells are not inordinately delayed within any phase of the cell cycle yet enough time is allowed for adequate repair of DNA lesions. In response to replication stress, ATR phosphorylates and activates Chk1 (Zhao, H. & Piwnica-Worms, H. Mol Cell Biol 21:4129-4139 (2001)); Chk1 then regulates a multitude of responses including intra-S phase checkpoint activation and HR-mediated repair (Bahassi, E. M. et al. Oncogene 27:3977-3985 (2008); Bartek, J. & Lukas, J. Cancer Cell 3:421-429 (2003); Feijoo, C. et al. J Cell Biol 154:913-923 (2001); Liu, Q. et al. Genes Dev 14:1448-1459 (2000); Sorensen, C. S. et al. Nat Cell Biol 7:195-201 (2005); Takai, H. et al. Genes Dev 14:1439-1447 (2000)). Chk1 impacts HR-mediated repair by promoting the key step of RAD51 recruitment to HR repair foci (Bahassi, E. M. et al. Oncogene 27:3977-3985 (2008); Sorensen, C. S. et al. Nat Cell Biol 7:195-201 (2005)). Because EBV-infected cells with functional STAT3 are deficient in activated (phosphorylated) Chk1 (Koganti, S. et al. Proc Natl Acad Sci USA 111:4946-4951 (2014)), experiments were conducted to determine whether RAD51 foci formation was also compromised. Using EBV-infected primary B cells from healthy subjects and patients with Job's syndrome (in whom the majority of STAT3 is nonfunctional despite normal levels of STAT3 protein (Holland, S. M. et al. N Engl J Med 357:1608-1619 (2007)), very few (2-3%) infected nuclei marked by EBV EBNA2 staining had RAD51 foci when STAT3 was functional. In contrast, >35% $EBNA2^+$ nuclei demonstrated RAD51 foci when STAT3 was impaired (~11 to 17-fold difference between STAT3-intact and STAT3-impaired cells; FIGS. 1A and 1B). Notably, there was only a 2-fold difference between percent cells in the S phase in STAT3-intact versus STAT3-impaired cells (FIG. 1C), consistent with our previous observation that EBV-infected STAT3-impaired cells arrest in the S phase (Koganti, S., et al. J Virol 88:516-524 (2014)). In a complementary approach, siRNA-mediated knockdown of STAT3 in EBV-transformed cells (LCL) demonstrated significant recovery of cells with RAD51 foci; no increase in $ATR^+$ cells was noted (FIGS. 1D and 1E). Furthermore, LCL with functional STAT3 recovered poorly from experimentally imposed DSBs compared to LCL with impaired STAT3 (FIGS. 1F and 1G). Thus, STAT3 curtails RAD51 nucleation and the cellular response to DSBs.

STAT3 Limits Homologous Recombination-Mediated DSB Repair through Chk1.

To determine if reduction in RAD51 foci-bearing cells indeed reflected poor HR-mediated repair or simply a dearth of DSBs, the ability of EBV-transformed cells and BL cells to repair a defined DSB was tested using a plasmid-based DR-GFP reporter assay (Nakanishi, K., et al. Methods Mol Biol 745:283-291 (2011); Nakanishi, K. et al. Nat Struct Mol Biol 18:500-503 (2011)). Both LCL and eBL cells showed very few (1-2.3%) repair competent cells despite transfection efficiencies >20% (FIGS. 2A, B, E, F, G, and J). Furthermore, in the presence of increasing concentrations of AG490, a Janus kinase inhibitor that has been shown to selectively inhibit STAT3 phosphorylation (Koganti, S., et al. J Virol 88:516-524 (2014); Koganti, S. et al. Proc Natl Acad Sci USA 111:4946-4951 (2014); Meydan, N. et al. Nature 379:645-648 (1996)), the percentages of $GFP^+$ cells simultaneously increased (FIGS. 2C, 2D, 2H, 2I, and 2K).

To address if STAT3 restricted HR-mediated repair via Chk1, AG490-exposed cells were examined for GFP expression in the presence of wild-type versus a phospho-dead (S345A) mutant of Chk1. While STAT3-impaired cells demonstrated HR-mediated DSB repair, repair was limited in the presence of the Chk1 mutant (FIGS. 2L-2O), indicating that a STAT3-Chk1 axis is responsible for disrupting HR-mediated repair in EBV-transformed cells.

EBV-Transformed Cells and EBV-Positive Burkitt Lymphoma Cells Exhibit BRCAness.

Given the defect in HR-mediated repair in EBV-transformed cells, the effect of Olaparib, a PARP inhibitor now in the clinic, on several LCL derived from healthy subjects and $EBV^+$ BL-derived lines was examined. Though typically used with other anti-cancer agents, Olaparib used alone demonstrated >50% reduction in growth of all LCL (FIGS. 3A-3C). The effect was more pronounced on BL lines which exhibited exquisite sensitivity to PARP inhibition (FIGS. 3B-3D). Thus, EBV-transformed cells and lymphoma lines known to have constitutively active STAT3 (Weber-Nordt, R. M. et al. Blood 88:809-816 (1996)) are susceptible to PARP inhibition.

EBV-Transformed Cells are Proficient in MMEJ-Mediated DSB Repair

Impaired HR-mediated repair in the face of oncogene-induced replication stress and reliance on PARP suggested that EBV-transformed cells utilized the error-prone mechanism of MMEJ to repair DSBs. During MMEJ-mediated repair, PARP facilitates recruitment of DNA polymerase theta to DSBs (Mateos-Gomez, P. A. et al. Nature 518:254-257 (2015)). LCL and BL cells were therefore tested for their ability to perform MMEJ-mediated DSB repair using the EJ2-GFP reporter assay (Bennardo, N., et al. PLoS Genet 4: e1000110 (2008)). Both types of cells demonstrated greater competence at repairing DSBs using MMEJ compared to HR (FIGS. 3I, 3J, 3M, and 3N).

A STAT3-Gene Signature to Predict Susceptibility of Cancers to PARP Inhibition.

With STAT3 constitutively active in a variety of cancers, a cross-analysis was performed between transcriptomic and PARP inhibitor susceptibility data from 452 cancer lines derived from a wide variety of tissues archived by the Cancer Genome Project, and a publically-available STAT3 ChIP-seq dataset from human cells by the ENCODE Project (Consortium, E. P. PLoS Biot 9: e1001046 (2011); Garnett, M. J. et al. Nature 483:570-575 (2012); Hill, E. R. et al. J Virol 87:11438-11446 (2013)). By comparing lines that were highly sensitive to PARP inhibition to those that were highly resistant, 27 STAT3-target genes were identified that were upregulated in all highly sensitive lines (FIG. 4A). Examination of expression of the 27 genes on hierarchically clustered binary plots (FIGS. 4B and 4C) resulted in identification of 9 genes with high expression in lines with low IC50s (i.e. in sensitive lines) but low expression in lines with high IC50s (i.e. in resistant lines). In parallel, Lasso and Elastic net regression analyses were also performed to identify four STAT3-target genes that were common between 3 models and the original 27 genes from above. Two of the four genes were distinct from the 9 gene subset. Together, they yielded a set of 11 genes (FIG. 4D). Performance of the STAT3 11-gene signature was tested on all cell lines and the ROC curve revealed an AUC of 0.804 (FIG. 4E). Thus, a small set of STAT3-target genes can predict susceptibility of a wide variety of cancer-derived lines to PARP inhibition.

Discussion

Constitutive activation or overexpression of STAT3 marks a large number of human cancers including EBV-related cancers (Yu, H. & Jove, R. Nat Rev Cancer 4:97-105 (2004); Nepomuceno, R. R., et al. Transplantation 74:396-402 (2002)). Mutations, frequently in genes that activate growth factor- and cytokine-signaling pathways activate STAT3 via receptor tyrosine kinases such as the Janus-activated kinase (JAK) family kinases or less often by nonreceptor kinases such as Src (Greenman, C. et al. Nature 446:153-158 (2007); Schindler, C. & Darnell, J. E., Jr. Annu Rev Biochem 64: 621-651 (1995); Silva, C. M. et al. Oncogene 23:8017-8023 (2004)). Using a system that had previously been exploited to demonstrate that STAT3 curbs DNA damage signaling by impairing phosphorylation of Chk1, this defect in Chk1 activation was shown to blunt HR-mediated repair. As a consequence, cells exhibit BRCAness resulting in susceptibility to PARP inhibition. These findings are germane in view of observations that cancer patients without detectable mutations in HR components also derive significant clinical benefit from PARP inhibitors (Mirza, M. R. et al. N Engl J Med 375:2154-2164 (2016)).

There is a recognized need for biomarkers that predict PARP inhibitor responses. Currently, HR-related mutation signatures including the recently published Signature 3, a few gene expression profiles applicable to breast and ovarian cancers, and a small number of HR assays are available for prediction of susceptibility to PARP inhibitors (Daemen, A. et al. Breast Cancer Res Treat 135:505-517 (2012); Konstantinopoulos, P. A. et al. J Clin Oncol 28:3555-3561 (2010); McGrail, D. J. et al. NPJ Syst Biol Appl 3:8 (2017); Polak, P. et al. Nat Genet 49:1476-1486 (2017); Severson, T. M. et al. Breast Cancer Res 19:99 (2017); Bitler, B. G., et al. Gynecol Oncol 147:695-704 (2017); Frey, M. K. & Pothuri, B. Gynecol Oncol Res Pract 4:4 (2017); Ledermann, J. et al. Lancet Oncol 15:852-861 (2014); Watkins, J. A., et al. Breast Cancer Res 16:211 (2014)). However, these are not yet completely inclusive of responders (Mirza, M. R. et al. N Engl J Med 375:2154-2164 (2016)). As more is learned about HR itself, additional predictive approaches will emerge. This study is an example that now links STAT3 activation to HR disruption. By doing so, it broadens the range of cancers that are likely to be susceptible to synthetic lethality beyond those derived from reproductive tissues. Since STAT3 is a transcriptional activator, it also allows prediction of susceptibility based on gene expression—prediction that now extends to multiple tissue types.

Of the 11 genes indicative of susceptibility to PARP inhibition, five are directly or indirectly linked to DNA repair or DNA damage signaling. SMARCAD1 was recently shown to mediate DNA end resection at DSBs for HR-mediated repair (Chakraborty, S. et al. iScience 2:123-135 (2018)). PRKX encodes a serine threonine protein kinase that phosphorylates MBD4/MED1, a DNA N-glycosylase involved in mismatch repair (Hendrich, B., et al. Nature 401:301-304 (1999); Petronzelli, F. et al. J Biol Chem 275:32422-32429 (2000); Wu, P. et al. J Biol Chem 278: 5285-5291 (2003)). MDM4/MDMX is known to regulate p53 and p73 and is itself regulated via phosphorylation by ATM, Chk1, and Chk2 (Chen, L., et al. EMBO J 24:3411-3422 (2005); Jin, Y. et al. EMBO J 25:1207-1218 (2006)). BLMH is a DNA-binding cysteine peptidase that mediates Bleomycin resistance (Zheng, W. & Johnston, S. A. Mol Cell Biol 18:3580-3585 (1998)). ZBTB40 is a zinc finger protein whose function is presently unknown; however, on a proteomic analysis, it was a target of phosphorylation by ATM/ATR in response to DNA damage (Matsuoka, S. et al. Science 316:1160-1166 (2007)). Little is known about the function of five other genes (ATXN2L, RBM33, ATP5G2, GPR75. ASB3, and ASPHD2). The last, AP4B1, is a protein that regulates vesicular transport of proteins (Hirst, J., et al. Mol Biol Cell 10:2787-2802 (1999); Dell'Angelica, E. C., et al. J Biol Chem 274:7278-7285 (1999)).

In terms of susceptibility of EBV-transformed cells to Olaparib, this drug is an inhibitor of PARP1 and 2, and MMEJ requires PARP1 to facilitate the recruitment of DNA polymerase theta to DNA lesions (Mateos-Gomez, P. A. et al. Nature 518:254-257 (2015); Bitler, B. G., et al. Gynecol Oncol 147:695-704 (2017)). Although this would suggest that susceptibility of EBV-transformed cells and lymphoma cells to Olaparib was a result of blocking MMEJ, additional contribution via impairment of other mechanisms such as base excision repair which uses PARP1-3 cannot be excluded.

In summary, STAT3, a prominent oncogene, has been linked to HR-mediated repair and BRCAness, thereby expanding the range of cancers likely to be susceptible to synthetic lethal approaches. STAT3, being a transcriptional activator, also allows prediction of such susceptibility based on gene expression.

Materials and Methods

Study Subjects

Blood was obtained from study subjects following informed consent. The study of human subjects was approved by the Institutional Review Boards at the University of Florida, Stony Brook University, and the National Institute of Allergy and Infectious Diseases. Healthy EBV-seronegative volunteers ranged from 18 to 28 years of age. Peripheral blood B cells were isolated and EBV-LCL were derived from three healthy subjects and three Job's syndrome patients. These were described in a previous publication (Koganti, S. et al. Proc Natl Acad Sci USA 111:4946-4951 (2014)).

Isolation of Primary B Lymphocytes and Infection with EBV

Peripheral blood B cells were isolated by negative selection and infections with EBV were performed as described (Koganti, S., et al. J Virol 88:516-524 (2014)).

Culture Conditions

Newly-infected B cells and previously established EBV-LCL were grown in culture using conditions described (Koganti, S., et al. J Virol 88:516-524 (2014)). For experiments using AG490 and Olaparib, chemicals were added to cultures at time 0. For experiments using Olaparib, the drug was supplemented at the initial concentration every fourth day. For experiments using Bleomycin, the drug was added for an hour, following which cells were washed and placed back in culture. We had previously demonstrated 50 μM AG490 to be minimally toxic to EBV-infected B-cell lines (Koganti, S., et al. J Virol 88:516-524 (2014); Koganti, S. et al. Proc Natl Acad Sci USA 111:4946-4951 (2014)).

Antibodies

The following primary antibodies were used for immunologic applications: rabbit anti-human STAT3, rabbit anti-human pSTAT3 (Y705), mouse anti-human RAD51, rabbit anti-human pATR (S428), mouse anti-human γH2AX, mouse anti-human β-actin, rat anti-(EBV)EBNA2 (clone R3) (Kremmer, E. et al. Virology 208:336-342 (1995)). Secondary antibodies included HRP-anti-mouse Ab, HRP-anti-rabbit Ab, FITC-anti-mouse IgG, PE-anti-rabbit IgG, and PE-anti-rat IgG.

Flow Cytometry

For assessment of cell-cycle distribution, cells were fixed, permeabilized, and stained with anti-EBNA2 antibody and 50 μg/ml propidium iodide supplemented with 1 μg/ml RNase A, as previously described (Hill, E. R. et al. J Virol 87:11438-11446 (2013)). For DR-GFP and EJ2-GFP assays, cells were transfected with the appropriate combinations of plasmids and harvested 48 hours later. Data were acquired using a FACS Calibur and analyzed using FlowJo software.

Immunofluorescence Microscopy

Cells were stained as for flow cytometry, washed, cytospun onto glass slides, air dried, and mounted with DAPI Prolong Gold Anti-fade (Life Technologies). Images were acquired at 40×magnification on an AxioScope Al microscope (Zeiss) with SPOT v4.0 software. When counting cells with nuclear foci, images were blinded and counted by two individuals; only nuclei with foci were considered positive.

Immunoblotting

Total extracts from $1\times10^6$ per mL cells were analyzed by immunoblotting as described (Hill, E. R. et al. J Virol 87:11438-11446 (2013)).

Plasmids, siRNAs, and Transfections

Plasmids DR-GFP, pCBASce (encoding I-Sce1 enzyme), and pCAGGS were gifts from Dr. Maria Jasin (Nakanishi, K. et al. Nat Struct Mol Biol 18:500-503 (2011)). EJ2-GFP-puro was a gift from Dr. Jeremy Stark (Addgene plasmid # 44025) (Bennardo, N., et al. PLoS Genet 4: e1000110 (2008)). Plasmids bearing wild-type and phosphorylation site Chk1 mutant S345A were gifts from Dr. Kum Kum Khanna (Gatei, M. et al. J Biol Chem 278:14806-14811 (2003)). BL cells and EBV-LCL were transfected using an Amaxa II nucleofector with plasmids or siRNA [targeting STAT3 (sc-29493) or scrambled (sc-37007), Santa Cruz Biotechnology] as previously described (King, C. A., Li, X., J Virol 89:11347-11355 (2015)).

Statistical Analysis

Unless stated otherwise, statistical significance was determined using p values that were calculated by comparing the means of two groups of interest using unpaired Student t test.

Analysis of Cancer Lines

Gene expression data from 452 cancer lines from a variety of tissue types from the Cancer Genome Project were examined; data were previously normalized using robust multi-array averaging (Garnett, M. J. et al. Nature 483:570-575 (2012)). Differential gene expression was examined between cancer lines that were highly sensitive (18 lines; corresponding to ~30% of sensitive lines) and highly resistant (23 lines. corresponding to ~10% of resistant lines) to PARP inhibition. We then determined which genes, predicted to be transcriptional targets of STAT3 (~8,000 genes from a publically-available STAT3 ChIP-seq) (Consortium, E. P. PLoS Biol 9: e1001046 (2011)), were upregulated in the highly sensitive lines compared to the highly resistant lines using limma-voom (Smyth, G. K. Limma: linear models for microarray data. 397-420 (Springer, New York, NY, 2005)) which estimates precision weights for linear modelling in the empirical Bayesian analysis pipeline and results in moderated t-statistics. Adjusted p-values were calculated and filtered using a false-discovery rate of 0.05. There were 699 differentially expressed genes upregulated in the highly sensitive lines. Of the 699 genes, 27 were upregulated in all highly sensitive lines relative to the mean resistant expression.

A hierarchically clustered binary plot of expression data of the 27 genes in all cell lines was generated using high or low calls that were determined based on whether expression exceeded the sensitive mean minus one standard deviation or not. A second binary plot was generated on an IC50 scale using the subpopulation of lines (indicated by a yellow bar; FIG. 4B) that expressed overall high levels of the 27 genes. Of these, nine genes with high expression in lines with low IC50s (i.e. high expression in sensitive lines) but low expression in lines with high IC50s (i.e. low expression in resistant lines) were selected.

In parallel, Lasso (120 steps with 5-fold cross validation) (Tibshirani, R. Journal of the Royal Statistical Society. Series B (Methodological) 58:267-288 (1996)) and Elastic net (Zou, H. Journal of the Royal Statistical Society: Series B (Statistical Methodology) 67:301-320 (2005)) analyses were run in SAS on the 8,000 STAT3-transcriptional targets using five distinct modeling parameter sets (5-fold 120-steps, 5-fold 500-steps, 10-fold 120-steps, 10-fold 500-steps) where the gene expression for the STAT3-transcriptional targets was used to predict IC50. All models performed similarly based on gene sets selected and root mean-squared error. From these analyses, four predictive genes were identified in common between the three models run for 120 steps and the 27 gene set from above. Two of these genes, which were good predictors of IC50, were distinct from the nine gene subset from above. These were added to the nine to make a total of 11 genes.

For the ROC curve, samples were binned by IC50 from zero to seven by 0.5 intervals individually for primarily red (i.e. lines expressed at overall high levels) and mixed zones as determined from the binary heatmap (FIG. 4B) where zones were delineated such that at least 60% of the genes were expressed at high level (red) or not (mixed). The percentage of samples falling into each bin were plotted in scatter plots with mixed zone percentages on the x-axis and red zone percentages on the y-axis. The plotted data were fit with a second order polynomial, and the area under the curve (AUC) was estimated from the fit equation by taking the integral from zero to one.

Example 2

Figure 5D:
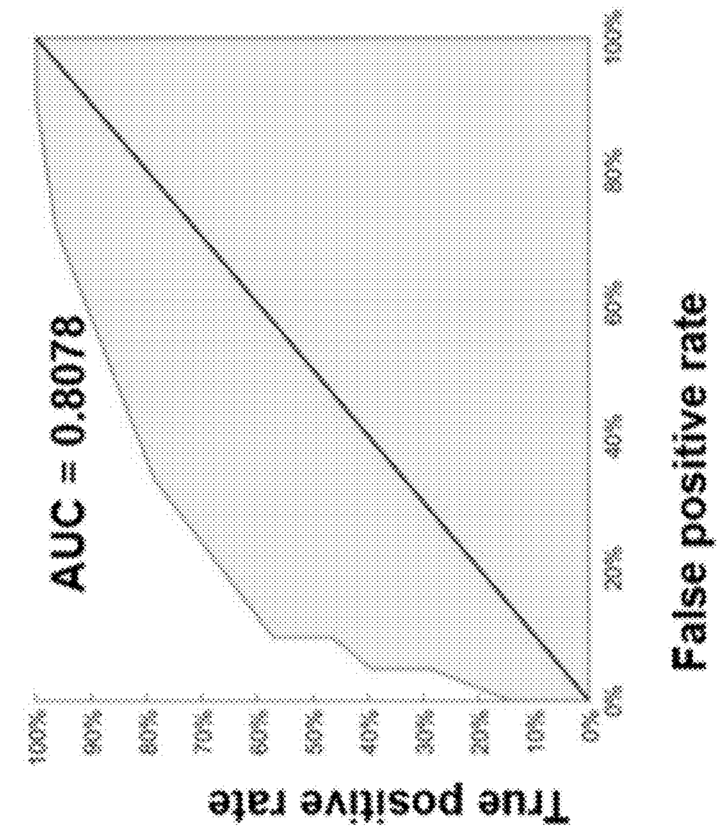

The predictive value of the STAT3 11 gene set was further assessed by receiver operating characteristic (ROC) curve analysis using normalized data from blood cancer lines represented among the 452 cancer cell lines in the Cancer Genome Project database (Garnett, M. J., et al. Nature, 483, 570-575). Once again, samples were binned by PARP inhibitor IC50 from zero to seven in 0.5 intervals individually for primarily red (i.e. lines expressed at overall high levels) and mixed zones. The percentage of samples falling into each bin were plotted in scatter plots with mixed zone percentages on the x-axis and red zone percentages on the y-axis. The ROC curves generated using all cancer lines (FIGS. 5A and 5C; at least 60% genes expressed at high level or not) versus blood cancer lines (FIGS. 5B and 5D; at least 82% genes expressed at high level or not) using the trapezoidal rule showed AUCs of 0.7825 and 0.8078, respectively, representing similar predictive values of the 11 gene set broadly and in relation to blood cancers.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for treating cancer in a subject, comprising
a) detecting in a sample from the subject elevated gene expression of at least SMARCAD1, PRKX, ZBTB40, ATXN2L, MDM4, AP4B1, RBM33, ATP5G2, BLMH, GPR75.ASB3, and ASPHD2; and
b) treating the subject with an effective dosage of a synthetic lethal therapy.

2. The method of claim 1, wherein the synthetic lethal therapy comprises a PARP (Poly ADP-ribose polymerase) inhibitor.

3. The method of claim 1, wherein the cancer comprises an ovarian or breast cancer.

4. The method of claim 1, wherein the cancer lacks BRCA1 or BRCA2 gene mutations.

5. The method of claim 1, further comprising assaying a sample from the subject for one or more gene mutation relating to homologous recombination (HR) repair.

6. The method of claim 5, wherein the gene mutation comprises a BRCA1 mutation, BRCA2 mutation, or a combination thereof.

7. The method of claim 1, wherein the sample comprises a tumor biopsy.

* * * * *

SEQUENCE LISTING

```
<160> NUMBER OF SEQ ID NOS: 36

<210> SEQ ID NO 1
<211> LENGTH: 25
<212> TYPE: DNA
<213> ORGANISM: Artificial Sequence
```

<220> FEATURE:
<223> OTHER INFORMATION: Synthetic Construct

<400> SEQUENCE: 1
gtgattatag tttctgagcc atctg 25

<210> SEQ ID NO 2
<211> LENGTH: 22
<212> TYPE: DNA
<213> ORGANISM: Artificial Sequence
<220> FEATURE:
<223> OTHER INFORMATION: Synthetic Construct

<400> SEQUENCE: 2
ccaattccga aaggtcttcc ag 22

<210> SEQ ID NO 3
<211> LENGTH: 26
<212> TYPE: DNA
<213> ORGANISM: Artificial Sequence
<220> FEATURE:
<223> OTHER INFORMATION: Synthetic Construct

<400> SEQUENCE: 3
aagagtccca aggccttcct accatg 26

<210> SEQ ID NO 4
<211> LENGTH: 24
<212> TYPE: DNA
<213> ORGANISM: Artificial Sequence
<220> FEATURE:
<223> OTHER INFORMATION: Synthetic Construct

<400> SEQUENCE: 4
gcgattagga aacatgaaga acgg 24

<210> SEQ ID NO 5
<211> LENGTH: 20
<212> TYPE: DNA
<213> ORGANISM: Artificial Sequence
<220> FEATURE:
<223> OTHER INFORMATION: Synthetic Construct

<400> SEQUENCE: 5
cttgggcacg atgggagctt 20

<210> SEQ ID NO 6
<211> LENGTH: 23
<212> TYPE: DNA
<213> ORGANISM: Artificial Sequence
<220> FEATURE:
<223> OTHER INFORMATION: Synthetic Construct

<400> SEQUENCE: 6
tccgctccgt ggactgggaa gct 23

<210> SEQ ID NO 7
<211> LENGTH: 22
<212> TYPE: DNA
<213> ORGANISM: Artificial Sequence
<220> FEATURE:
<223> OTHER INFORMATION: Synthetic Construct

<400> SEQUENCE: 7
tcagtcccgg ccattgaaat at 22

-continued

<210> SEQ ID NO 8
<211> LENGTH: 24
<212> TYPE: DNA
<213> ORGANISM: Artificial Sequence
<220> FEATURE:
<223> OTHER INFORMATION: Synthetic Construct

<400> SEQUENCE: 8
ccttagtaag gacaccaatg tatg 24

<210> SEQ ID NO 9
<211> LENGTH: 28
<212> TYPE: DNA
<213> ORGANISM: Artificial Sequence
<220> FEATURE:
<223> OTHER INFORMATION: Synthetic Construct

<400> SEQUENCE: 9
catcagtccc ggccattgaa atatgttt 28

<210> SEQ ID NO 10
<211> LENGTH: 20
<212> TYPE: DNA
<213> ORGANISM: Artificial Sequence
<220> FEATURE:
<223> OTHER INFORMATION: Synthetic Construct

<400> SEQUENCE: 10
cggcctggcc ttagctcttt 20

<210> SEQ ID NO 11
<211> LENGTH: 19
<212> TYPE: DNA
<213> ORGANISM: Artificial Sequence
<220> FEATURE:
<223> OTHER INFORMATION: Synthetic Construct

<400> SEQUENCE: 11
atgcgggaag ggcctccat 19

<210> SEQ ID NO 12
<211> LENGTH: 23
<212> TYPE: DNA
<213> ORGANISM: Artificial Sequence
<220> FEATURE:
<223> OTHER INFORMATION: Synthetic Construct

<400> SEQUENCE: 12
cacctcgtgg ccctcaccat ctg 23

<210> SEQ ID NO 13
<211> LENGTH: 26
<212> TYPE: DNA
<213> ORGANISM: Artificial Sequence
<220> FEATURE:
<223> OTHER INFORMATION: Synthetic Construct

<400> SEQUENCE: 13
gaaatgttca ctgttaaaga ggtcat 26

<210> SEQ ID NO 14
<211> LENGTH: 22
<212> TYPE: DNA
<213> ORGANISM: Artificial Sequence
<220> FEATURE:
<223> OTHER INFORMATION: Synthetic Construct

<400> SEQUENCE: 14
gcatatcata gagagggctt gg 22

<210> SEQ ID NO 15
<211> LENGTH: 26
<212> TYPE: DNA
<213> ORGANISM: Artificial Sequence
<220> FEATURE:
<223> OTHER INFORMATION: Synthetic Construct

<400> SEQUENCE: 15
tctttcacgg agaagctctg acgtcc 26

<210> SEQ ID NO 16
<211> LENGTH: 20
<212> TYPE: DNA
<213> ORGANISM: Artificial Sequence
<220> FEATURE:
<223> OTHER INFORMATION: Synthetic Construct

<400> SEQUENCE: 16
gaatgtgcag caggtgctag 20

<210> SEQ ID NO 17
<211> LENGTH: 20
<212> TYPE: DNA
<213> ORGANISM: Artificial Sequence
<220> FEATURE:
<223> OTHER INFORMATION: Synthetic Construct

<400> SEQUENCE: 17
cataggtggc attgccagga 20

<210> SEQ ID NO 18
<211> LENGTH: 25
<212> TYPE: DNA
<213> ORGANISM: Artificial Sequence
<220> FEATURE:
<223> OTHER INFORMATION: Synthetic Construct

<400> SEQUENCE: 18
agcttcgagg gtactgcacg gatgt 25

<210> SEQ ID NO 19
<211> LENGTH: 24
<212> TYPE: DNA
<213> ORGANISM: Artificial Sequence
<220> FEATURE:
<223> OTHER INFORMATION: Synthetic Construct

<400> SEQUENCE: 19
acttggagaa gatttgctat ctgg 24

<210> SEQ ID NO 20
<211> LENGTH: 25
<212> TYPE: DNA
<213> ORGANISM: Artificial Sequence
<220> FEATURE:
<223> OTHER INFORMATION: Synthetic Construct

<400> SEQUENCE: 20
gtaacaccct gagaactgaa atttt 25

<210> SEQ ID NO 21

<211> LENGTH: 27
<212> TYPE: DNA
<213> ORGANISM: Artificial Sequence
<220> FEATURE:
<223> OTHER INFORMATION: Synthetic Construct

<400> SEQUENCE: 21
atcagtcgga tttgtcagat gaagagc 27

<210> SEQ ID NO 22
<211> LENGTH: 20
<212> TYPE: DNA
<213> ORGANISM: Artificial Sequence
<220> FEATURE:
<223> OTHER INFORMATION: Synthetic Construct

<400> SEQUENCE: 22
ccactccctc cttggtcaag 20

<210> SEQ ID NO 23
<211> LENGTH: 19
<212> TYPE: DNA
<213> ORGANISM: Artificial Sequence
<220> FEATURE:
<223> OTHER INFORMATION: Synthetic Construct

<400> SEQUENCE: 23
ccaagctgct gaggctctc 19

<210> SEQ ID NO 24
<211> LENGTH: 25
<212> TYPE: DNA
<213> ORGANISM: Artificial Sequence
<220> FEATURE:
<223> OTHER INFORMATION: Synthetic Construct

<400> SEQUENCE: 24
tgtcagtatc tccggtcgtt tcagc 25

<210> SEQ ID NO 25
<211> LENGTH: 19
<212> TYPE: DNA
<213> ORGANISM: Artificial Sequence
<220> FEATURE:
<223> OTHER INFORMATION: Synthetic Construct

<400> SEQUENCE: 25
agctcagggc gatgctgga 19

<210> SEQ ID NO 26
<211> LENGTH: 22
<212> TYPE: DNA
<213> ORGANISM: Artificial Sequence
<220> FEATURE:
<223> OTHER INFORMATION: Synthetic Construct

<400> SEQUENCE: 26
taacagcgtt caaccttgtc cc 22

<210> SEQ ID NO 27
<211> LENGTH: 28
<212> TYPE: DNA
<213> ORGANISM: Artificial Sequence
<220> FEATURE:
<223> OTHER INFORMATION: Synthetic Construct

<400> SEQUENCE: 27
cttgtctgaa tgttatgagg cttccatt 28

<210> SEQ ID NO 28
<211> LENGTH: 20
<212> TYPE: DNA
<213> ORGANISM: Artificial Sequence
<220> FEATURE:
<223> OTHER INFORMATION: Synthetic Construct

<400> SEQUENCE: 28
cgatgatgcc tctagtcctg 20

<210> SEQ ID NO 29
<211> LENGTH: 22
<212> TYPE: DNA
<213> ORGANISM: Artificial Sequence
<220> FEATURE:
<223> OTHER INFORMATION: Synthetic Construct

<400> SEQUENCE: 29
catttgtttg accagtctgc cg 22

<210> SEQ ID NO 30
<211> LENGTH: 21
<212> TYPE: DNA
<213> ORGANISM: Artificial Sequence
<220> FEATURE:
<223> OTHER INFORMATION: Synthetic Construct

<400> SEQUENCE: 30
tcatccagag cggcaggcgg a 21

<210> SEQ ID NO 31
<211> LENGTH: 23
<212> TYPE: DNA
<213> ORGANISM: Artificial Sequence
<220> FEATURE:
<223> OTHER INFORMATION: Synthetic Construct

<400> SEQUENCE: 31
atccgatgcc atttaggtct gaa 23

<210> SEQ ID NO 32
<211> LENGTH: 20
<212> TYPE: DNA
<213> ORGANISM: Artificial Sequence
<220> FEATURE:
<223> OTHER INFORMATION: Synthetic Construct

<400> SEQUENCE: 32
ccatcctctg ctgaaccttc 20

<210> SEQ ID NO 33
<211> LENGTH: 23
<212> TYPE: DNA
<213> ORGANISM: Artificial Sequence
<220> FEATURE:
<223> OTHER INFORMATION: Synthetic Construct

<400> SEQUENCE: 33
ctccaaatgg ctgtgagctg gtg 23

<210> SEQ ID NO 34
<211> LENGTH: 20
<212> TYPE: DNA

-continued

<213> ORGANISM: Artificial Sequence
<220> FEATURE:
<223> OTHER INFORMATION: Synthetic Construct

<400> SEQUENCE: 34
ggcacagctg gagcaggtat 20

<210> SEQ ID NO 35
<211> LENGTH: 22
<212> TYPE: DNA
<213> ORGANISM: Artificial Sequence
<220> FEATURE:
<223> OTHER INFORMATION: Synthetic Construct

<400> SEQUENCE: 35
cttcagcatg tcaggcaaaa tc 22

<210> SEQ ID NO 36
<211> LENGTH: 24
<212> TYPE: DNA
<213> ORGANISM: Artificial Sequence
<220> FEATURE:
<223> OTHER INFORMATION: Synthetic Construct

<400> SEQUENCE: 36
atccgtggca gcaaaatccg cttt 24